(12) United States Patent
Small et al.

(10) Patent No.: US 12,109,276 B2
(45) Date of Patent: Oct. 8, 2024

(54) NEAR-INFRARED DYES AND CONJUGATES FOR TARGETING TUMORS

(71) Applicant: Lahjavida, LLC, Colorado Springs, CO (US)

(72) Inventors: Lyle D. Small, Colorado Springs, CO (US); Ruizheng Wang, Colorado Springs, CO (US); Shane M. Crippen, Colorado Springs, CO (US)

(73) Assignee: Lahjavida, LLC, Colorado Springs, CO (US)

( * ) Notice: Subject to any disclaimer, the term of this patent is extended or adjusted under 35 U.S.C. 154(b) by 0 days.

(21) Appl. No.: 16/816,118

(22) Filed: Mar. 11, 2020

(65) Prior Publication Data

US 2020/0289676 A1    Sep. 17, 2020

Related U.S. Application Data

(60) Provisional application No. 62/819,146, filed on Mar. 15, 2019.

(51) Int. Cl.
| | |
|---|---|
| *A61B 5/00* | (2006.01) |
| *A61B 8/00* | (2006.01) |
| *A61B 10/00* | (2006.01) |
| *A61K 9/51* | (2006.01) |
| *A61K 31/704* | (2006.01) |
| *A61K 49/00* | (2006.01) |
| *C09B 23/01* | (2006.01) |

(52) U.S. Cl.
CPC ............ *A61K 49/0032* (2013.01); *A61K 9/51* (2013.01); *A61K 31/704* (2013.01); *A61K 49/0056* (2013.01); *C09B 23/0066* (2013.01)

(58) Field of Classification Search
CPC .... A61K 49/0032; A61K 9/51; A61K 31/704; A61K 49/0056; A61K 9/5094; A61K 41/0052; A61K 41/0071; A61K 47/545; A61K 49/085; A61K 49/183; C09B 23/0066; C09B 23/0016; C09B 23/086; C09B 47/00; C09B 69/008; A61P 35/00
See application file for complete search history.

(56) References Cited

U.S. PATENT DOCUMENTS

| | | | |
|---|---|---|---|
| 4,226,164 A | 10/1980 | Carter | |
| 10,030,036 B2 * | 7/2018 | Krutak | ............... A61K 49/0032 |
| 2008/0160090 A1 | 7/2008 | Oraevsky et al. | |
| 2009/0025977 A1 | 1/2009 | Anderson et al. | |
| 2010/0022449 A1 * | 1/2010 | Achilefu | ............... C09B 23/086 514/1.1 |
| 2011/0085974 A1 | 4/2011 | Chung et al. | |
| 2011/0250146 A1 * | 10/2011 | Zhang | ............... G01N 33/54326 424/9.34 |
| 2012/0251453 A1 | 10/2012 | Fukuda et al. | |
| 2013/0039858 A1 | 2/2013 | Brown et al. | |
| 2015/0376209 A1 * | 12/2015 | Krutak | ............... A61K 49/0032 607/101 |
| 2016/0281082 A1 * | 9/2016 | Lellouche | ............ C12N 15/113 |
| 2018/0353913 A1 | 12/2018 | Link et al. | |

FOREIGN PATENT DOCUMENTS

| | | | |
|---|---|---|---|
| JP | 2014525914 A | 10/2014 | |
| KR | 10-2016-0088830 | 7/2016 | |
| WO | 2009/012109 | 1/2009 | |
| WO | WO 2006/019775 A1 | 1/2009 | |
| WO | WO-2016106324 A1 * | 6/2016 | ........... A61K 47/558 |
| WO | 2017/201089 A1 | 11/2017 | |

OTHER PUBLICATIONS

Park et al. (Adv. Mater. 2008, 20, 1630-1635).*
Sato et al. (Spectrochimica Acta Part A 2009, 71, 2030-2039).*
Tan et al. (Biomater. 2012, 33, 2230-2239).*
Jiao et al. (Chem. Commun. 2018, 54, 9198-9201).*
Tong et al. Nanoletters 2011, 11, 3720-3726.*
Beik et al. (J. Control Release 2016, 235, 205-221).*
Lee et al. (Scientific Reports 2017, 7, p. 1-14).*
Yang et al. (Clin. Cancer Res. 2010, 16, 2833-2844).*
Tong et al. Nanolett. 2011, 11, 3720-3726).*
Biek et al. (J. Control. Release 2016, 235, 205-221).*
Wang et al. (Langmuir 2014, 30, 6197-6208).*
U.S. Appl. No. 61/178,835, filed May 15, 2009, Henary et al.
U.S. Appl. No. 61/309,282, filed 2010.
PCT International Patent Application No. PCT/US20/22668, International Search Report and Written Opinion of the International Searching Authority dated Jul. 6, 2020, 11 pages.
U.S. Appl. No. 12/778,569, Office Action mailed Mar. 4, 2016.
U.S. Appl. No. 12/778,569, Office Action mailed Jul. 19, 2016.
U.S. Appl. No. 12/778,569, Office Action mailed Jun. 9, 2017.
U.S. Appl. No. 12/778,569, Notice of Allowance mailed Jun. 13, 2018.
Cooper et al. The Use of Heptamethine Cyanine Dyes as Drug-Conjugate Systems in the Treatment of Primary and Metastatic Brain Tumors. Frontiers in Oncology, Jun. 2021, vol. 11, Article 654921, 16 pages.
Fu et al. Plasmonic Enhancement of Single-Molecule Fluorescence Near a Silver Nanoparticle. J Fluoresc., Nov. 2007; 17(6):811-816.
Pham et al. Synthesis and Application of a Water-Soluble Near-Infrared Dye for Cancer Detection Using Optical Imaging. Bioconjugate Chem., Apr. 2005, 16(3):735-740.
Pubchem. Substance Record for SIDS 135686945. Available Date May 28, 2012 [retrieved on Jun. 15, 2020] from the Internet, https://pubchem.ncbi.nim.nih.gov/substance/135686945.

(Continued)

*Primary Examiner* — Michael G. Hartley
*Assistant Examiner* — Melissa J Perreira
(74) *Attorney, Agent, or Firm* — Craig R. Miles; CR MILES P.C.

(57) ABSTRACT

The design, synthesis, and functionalization of a conjugate including a tumor-targeting near-infrared (NIR) dye and a therapeutic agent and/or a diagnostic agent, whereby the NIR dye can function to target the therapeutic agent and/or diagnostic agent to tumor cells.

12 Claims, 7 Drawing Sheets

(56) References Cited

OTHER PUBLICATIONS

Yang et al. Near IR Heptamethine Cyanine Dye-Mediated Cancer Imaging. Clin. Cancer Res., May 2010, 16(10):2833-2844.

Ali et al. Efficacy, long-term toxicity, and mechanistic studies of gold nanorods photothermal therapy of cancer in xenograft mice. Proceedings of the National Academy of Sciences, Mar. 2017, 114(15):E3110-E3118.

Alrahili et al. Absorption cross section of gold nanoparticles based on NIR laser heating and thermodynamic calculations. Scientific Reports, Nov. 2020, 10, article No. 18790.

Alrahili et al. Morphology Dependence in Photothermal Heating of Gold Nanomaterials with Near-Infrared Laser. J. Phys. Chem. C, Feb. 2020, 124(8):4755-4763.

Bevilacqua et al. Antifouling Strategies of Nanoparticles for Diagnostic and Therapeutic Application: A Systematic Review of the Literature. Nanomaterials, Mar. 2021, 11(3):780.

Chichel et al. Hyperthermia—description of a method and a review of clinical applications. Rep Pract Oncol Radiother, Oct. 2007, 12(15):267-275.

Choi et al. Heptamethine Cyanine Dye Mediated Drug Delivery: Hype or Hope. Bioconjug. Chem., Jun. 2020, 31(7):1724-1739.

Fan et al. Nanotechnology for Multimodal Synergistic Cancer Therapy. Chem. Rev., Nov. 2017, 117(22):13566-13638.

García et al. Zwitterionic-Coated "Stealth" Nanoparticles for Biomedical Applications: Recent Advances in Countering Biomolecular Corona Formation and Uptake by the Mononuclear Phagocyte System. Small, Jul. 2014 (published online Mar. 2014), 10(13):2516-2529.

Hirsch et al. Nanoshell-mediated near-infrared thermal therapy of tumors under magnetic resonance guidance. PNAS, Nov. 2003, 100(23):13549-13554.

Huang et al. Applications of gold nanorods for cancer imaging and photothermal therapy. Cancer nanotechnology. Methods Mol Biol, Jan. 2010, 624:343-357.

Huang et al. Folic acid-conjugated silica-modified gold nanorods for X-ray/CT imaging-guided dual-mode radiation and photothermal therapy. Biomaterials Dec. 2011, 32(36):9796-9809.

Huang et al. Plasmonic photothermal therapy (PPTT) using gold nanoparticles. Lasers in medical science, Jul. 2008 (published online Aug. 2007), 23(3):217-228.

Jauffred et al. Plasmonic Heating of Nanostructures. Chem. Rev., May 2019, 119(13):8087-8130.

Li et al. RGD-conjugated dendrimer-modified gold nanorods for in vivo tumor targeting and photothermal therapy. Molecular pharmaceutics, 2010 (published on Web Nov. 2009), 7(1):94-104.

Raoof et al. Gold Nanoparticles and Radiofrequency in Experimental Models for Hepatocellular Carcinoma. Nanomedicine, Aug. 2014, 10(6):1121-1130.

Rastinehad et al. Gold nanoshell-localized photothermal ablation of prostate tumors in a clinical pilot device study. PNAS, Sep. 2019, 116(37):18590-18596.

Savchuk et al. Size-dependent emission of a dipole coupled to a metal nanoparticle. MRS Advances, Nov. 2020, 5(62):3315-3325.

Shi et al. Heptamethine carbocyanine dye-mediated near-infrared imaging of canine and human cancers through the HIF-1α/OATPs signaling axis. Oncotarget, Oct. 2014, 5(20):10114-26.

Corresponding Japanese Patent Application No. 2021-555580, Office Action dated May 11, 2023, 6 pages.

Corresponding Canadian Patent Application No. 3,133,750, Office Action dated Mar. 29, 2023, 4 pages.

Corresponding European Patent Application No. 20774094.5, Supplementary European search Report dated Feb. 2, 2023, 12 pages.

Luo et al. Multifunctional Photosensitizer Grafted on Polyethylene Glycol and Polyethylenimine Dual-Functionalized Nanographene Oxide for Cancer-Targeted Near-Infrared Imaging and Synergistic Phototherapy. Applied Materials & Interfaces, Jul. 2016, 8(27):17176-17186.

Luo et al. A review of NIR dyes in cancer targeting and imaging. Biomaterials, Jul. 2011, 32(29):7127-7138.

Yeh et al. Tumor targeting and MR imaging with lipophilic cyanine-mediated near-infrared responsive porous Gd silicate nanoparticles. Biomaterials, Jul. 2013, 34(22):5677-88.

Zhang et al. pH- and Enzyme-Sensitive IR820-Paclitaxel Conjugate Self-Assembled Nanovehicles for Near-Infrared Fluorescence Imaging-Guided Chemo-Photothermal Therapy. Applied Materials & Interfaces, Sep. 2018, 10(36):30092-30102.

Zhou et al. Superstable Magnetic Nanoparticles in Conjugation with Near-Infrared Dye as a Multimodal Theranostic Platform. Applied Materials & Interfaces, Feb. 2016, 8(7):4424-33.

Corresponding Japanese Patent Application No. 2021- 555580, Office Action dated Jan. 4, 2024, 14 pages (with English translation).

Corresponding Canadian Patent Application No. 3,133,750, Office Action dated Sep. 8, 2023, 5 pages.

Corresponding Canadian Patent Application No. 3,133,750, Office Action dated Jan. 25, 2024, 3 pages.

Corresponding Brazilian Patent Application No. BR1120210182292, Office Action dated May 14, 2024, 7 pages.

* cited by examiner

NEAR-INFRARED DYES AND CONJUGATES FOR TARGETING TUMORS

I. BACKGROUND

There remains a need for a targeted cancer therapeutic agent with maximal efficacy in treating or killing tumor cells but minimal toxicity toward non-tumor or healthy cells. Additionally, there remains a need for a targeted cancer diagnostic agent.

II. SUMMARY OF THE INVENTION

Generally, the instant invention details the use of tumor-targeting near-infrared (NIR) dyes in conjunction with a variety of therapeutic agents. In particular, the instant invention discloses the use of metal nanoparticles, magnetic nanoparticles, so-called "lossy dielectric materials," chemotherapeutic agents, nitroxide radicals, photodynamic therapy agents, and photothermal therapy agents conjugated with a tumor-targeting NIR dye as a potentially effective treatment for various cancers. The NIR dye can target only malignant, cancerous cells in the body, bypassing healthy tissues, and can deliver the therapeutic agent to the appropriate site in the body, thus preventing or minimizing the harmful side-effects of many conventional cancer treatments when used without tumor-targeting technology.

Following, a broad object of a particular embodiment of the invention can be to provide a conjugate including a tumor-targeting NIR dye and a therapeutic agent, whereby the NIR dye can function to target and/or deliver the therapeutic agent to tumor cells.

Another broad object of a particular embodiment of the invention can be to provide a conjugate including a tumor-targeting NIR dye and a diagnostic agent, whereby the NIR dye can function to target and/or deliver the diagnostic agent to tumor cells.

Another broad object of a particular embodiment of the invention can be to provide a method of treating or killing tumor cells by targeting a conjugate including a tumor-targeting NIR dye and a therapeutic agent to tumor cells.

Another broad object of a particular embodiment of the invention can be to provide a method of diagnosing the presence of tumor cells by targeting a conjugate including a tumor-targeting NIR dye and a diagnostic agent to tumor cells, if present.

Naturally, further objects of the invention are disclosed throughout other areas of the specification, drawings, photographs, and claims.

III. A BRIEF DESCRIPTION OF THE DRAWINGS

IV. DETAILED DESCRIPTION OF THE PREFERRED EMBODIMENTS

The instant invention may provide an effective and versatile delivery method which combines tumor-targeting near-infrared (NIR) dyes with various cancer therapeutic agents and/or cancer diagnostic agents for (i) targeting tumor cells and/or (ii) killing tumor cells and/or (iii) imaging tumor cells.

As to particular embodiments, the instant invention may combine tumor-targeting fluorescent NIR dyes with various agents to create conjugates for the treatment and/or detection of various cancers, whereby these conjugates could be delivered directly to the tumor site, in contrast to conventional agents which may be non-specifically delivered and thus, may cause significant adverse side effects. Following, these conjugates may provide (i) a variety of effective therapeutic modalities, and/or (ii) a variety of diagnostic modalities, for example with NIR imaging. The former can include hyperthermia therapy via electromagnetic radiation using metal nanoparticles (such as gold nanoparticles) and/or magnetic nanoparticles (such as iron oxide nanoparticles), chemical therapy via chemotherapeutic agents (which may include conventional chemotherapeutics), nitroxide radicals, photodynamic therapy via NIR laser irradiation, and/or photothermal therapy via laser irradiation, whereby the deep penetration property of the irradiation can make this therapy widely applicable, regardless of the site of the tumor.

Figure 1:
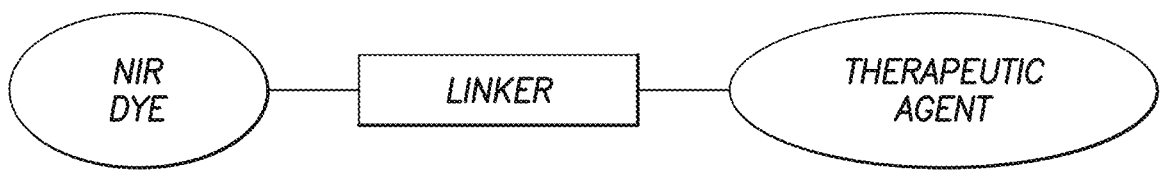
FIG. 1 is an illustration of a particular embodiment of a conjugate contemplated by the instant invention.
Figure 2:
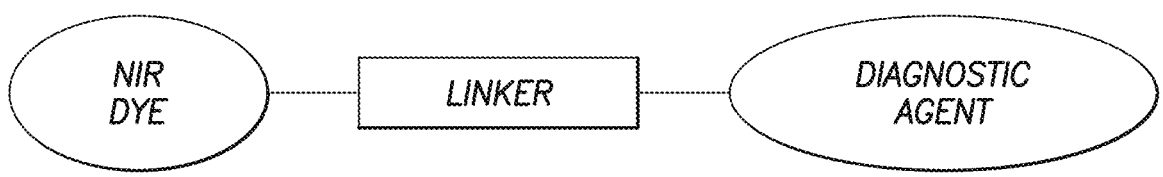
FIG. 2 is an illustration of a particular embodiment of a conjugate contemplated by the instant invention.

As to particular embodiments, the instant invention may include novel compositions or conjugates which comprise a tumor-targeting fluorescent NIR dye, such as a tumor-targeting fluorescent cyanine dye, and a therapeutic or diagnostic agent covalently bound to the NIR dye via a linker, as shown in FIGS. 1 and 2, respectively.

As to particular embodiments, the NIR dye can have Formula I as follows:

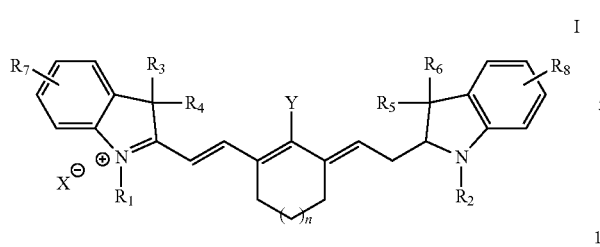

I wherein n can be 0 or 1, and Y can be Cl, substituted C, O, S, or N.

As to particular embodiments, the NIR dye can have an absorption wavelength in the region of 650 nm to 1200 nm.

As to particular embodiments, the NIR dye can be symmetrical. As but one illustrative example, a particular embodiment of a symmetrical NIR dye which may be useful with the instant invention can be synthesized according to Scheme I below.

As to other particular embodiments, the NIR dye can be asymmetrical. As but one illustrative example, a particular embodiment of an asymmetrical NIR dye which may be useful with the instant invention can be synthesized according to Scheme II below.

Scheme I

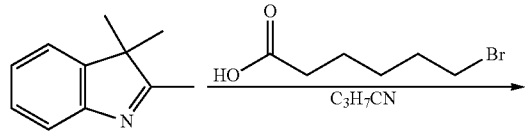

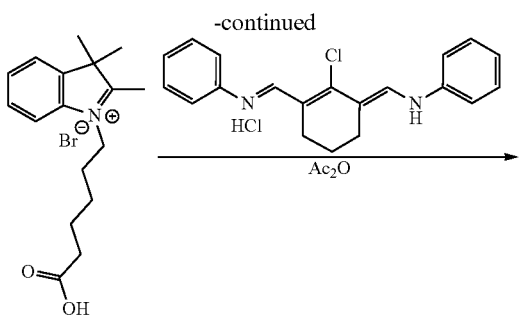

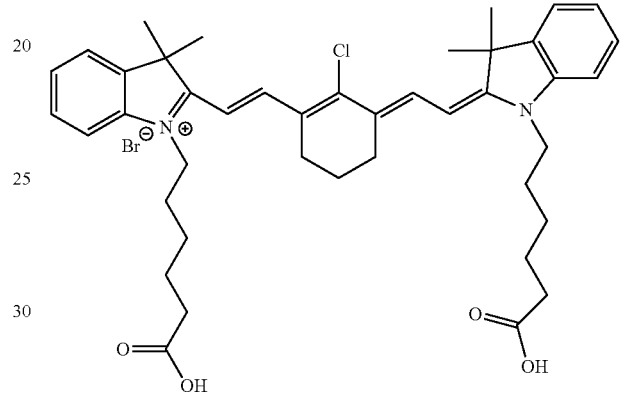

Scheme II

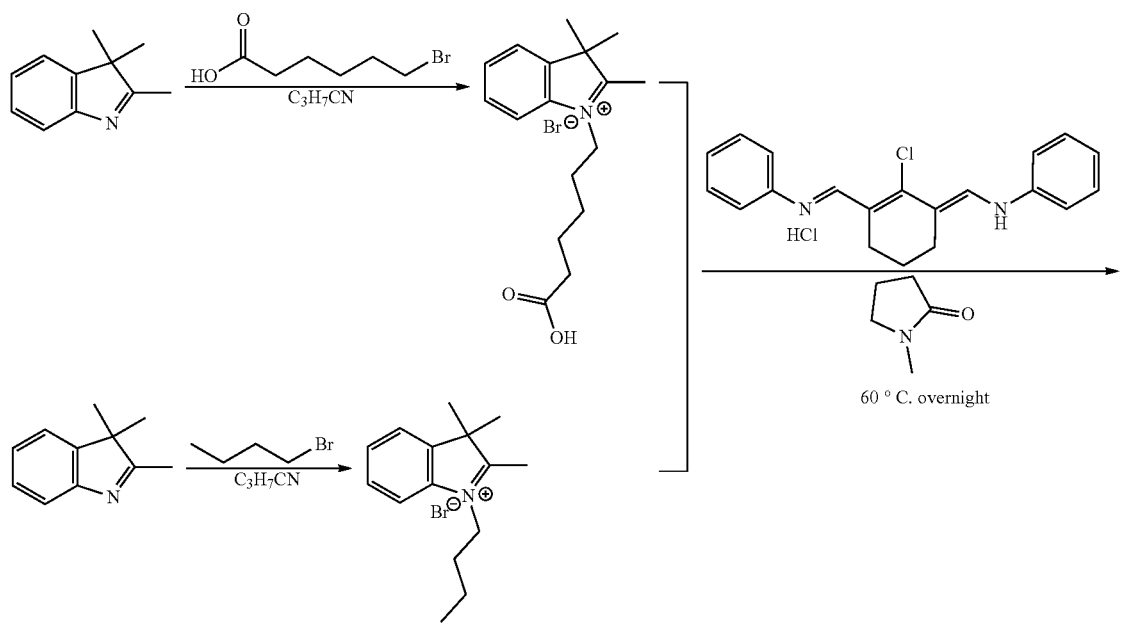

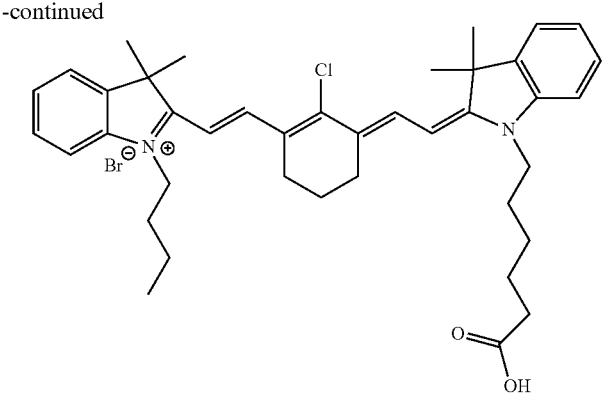

There may be multiple sites on the NIR dye where a therapeutic or diagnostic agent can be attached via a linker. For example, a linking site can be via the central ring (such as the central cyclohexyl ring), via the nitrogen of an indole moiety, via a geminal position, or via an aromatic ring. As to particular embodiments, one or more of $R_1$-$R_8$ or Y as shown in Formula I can be used as a linking site to covalently attach the linker and the therapeutic or diagnostic agent to the NIR dye to form the instant conjugate.

As to particular embodiments, the linking site can be via the central cyclohexyl ring using the reactive chlorine substituted by carbon, oxygen, sulfur, or nitrogen derivatives, as shown in Formula II as follows:

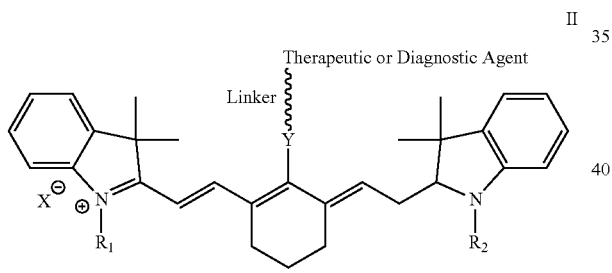

II

As but one illustrative example, a particular embodiment of an NIR dye having a reactive functional group on the central cyclohexyl ring which may be useful with the instant invention can be synthesized according to Scheme III below:

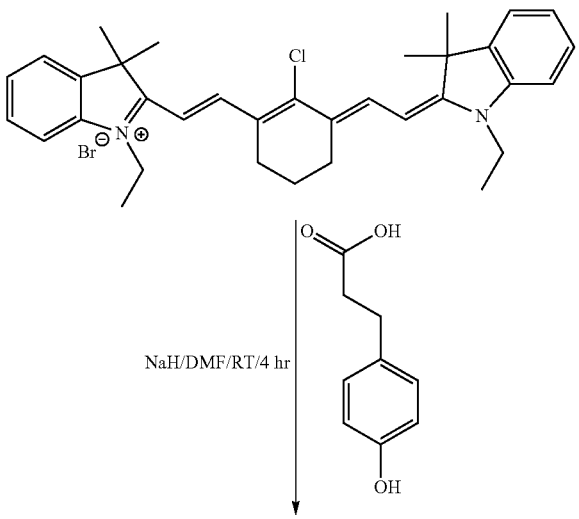

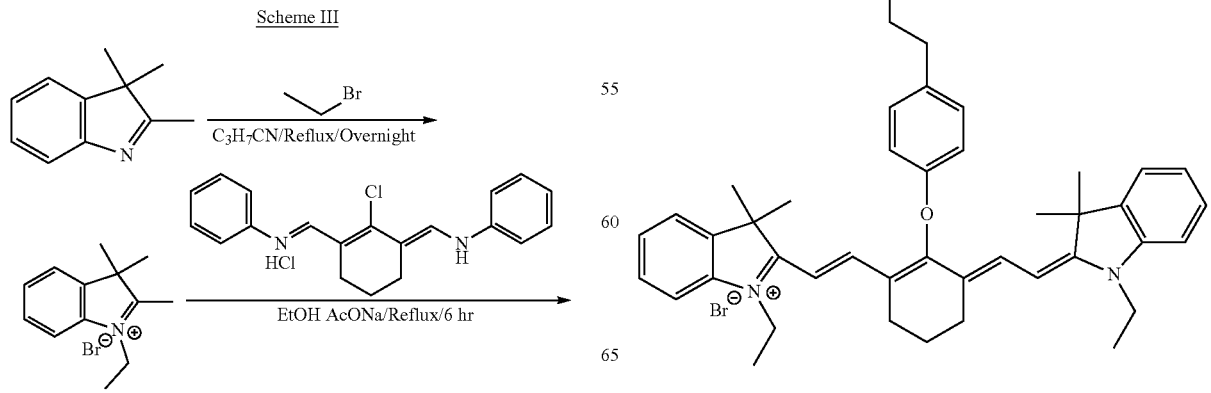

As to other particular embodiments, the linking site can be via the nitrogen of an indole moiety, whereby the therapeutic or diagnostic agent can be either mono- or bis-linked, as shown in Formula III as follows:

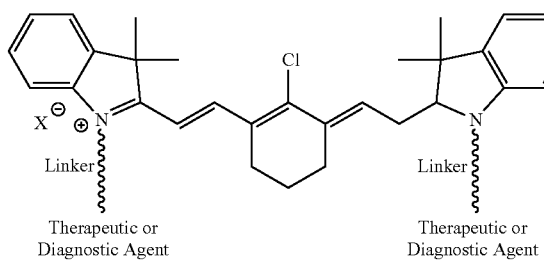

III

As but one illustrative example, a particular embodiment of an NIR dye having a linking site via the nitrogen of an indole moiety which may be useful with the instant invention can be synthesized according to Scheme IV below:

Scheme IV

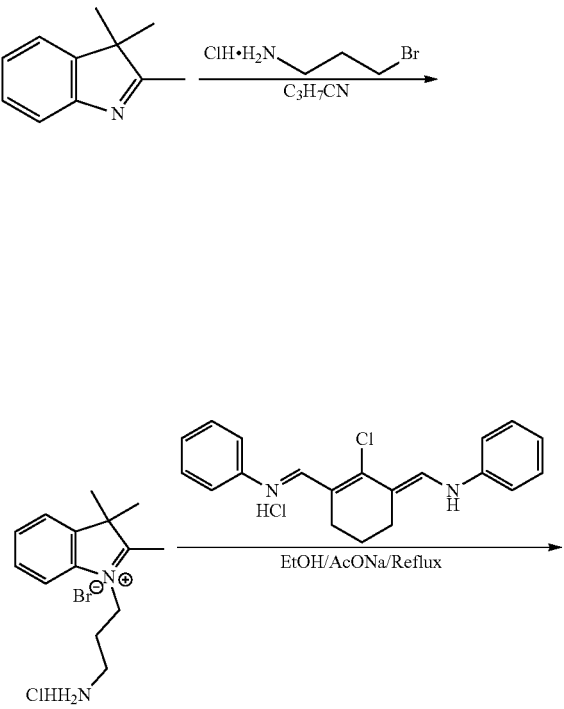

-continued

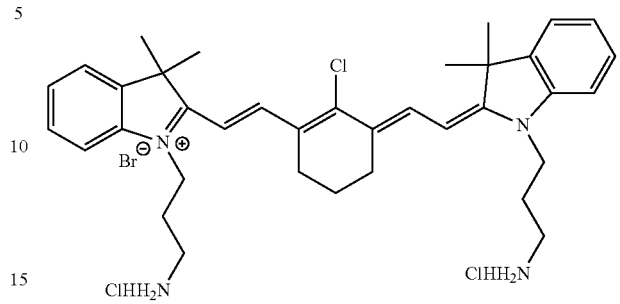

Therapeutic Modalities

Various therapeutic modalities can be used in accordance with the instant invention. Regarding hyperthermia therapy, a metal nanoparticle, which can function as a hyperthermia agent, may be useful as a therapeutic agent when conjugated to an NIR dye, as per the instant invention, which may be supported by U.S. Pat. No. 10,030,036, which is hereby incorporated by reference in its entirety herein. As but one illustrative example, a metal nanoparticle can comprise a gold (Au) nanoparticle.

Figure 3:
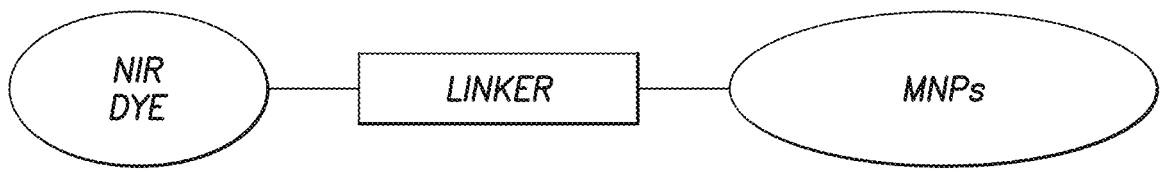
FIG. 3 is an illustration of a particular embodiment of a conjugate contemplated by the instant invention.

Now referring primarily to FIG. 3, as to particular embodiments, a magnetic nanoparticle (MNP), which can function as a hyperthermia agent, may be useful as a therapeutic agent when conjugated to an NIR dye, as per the instant invention; following, the MNP-NIR dye conjugate can be targeted to tumor cells, as per the instant invention.

MNPs, which may include materials based in iron oxide nanoparticles (IONPs), such as $Fe_3O_4$, or materials such as FeCo, FePt, or $Fe_{1-x}Si_x$, may be useful both (i) as a diagnostic agent (for example, as a magnetic resonance imaging (MM) contrast material) and/or (ii) as a therapeutic agent to treat deep tissue tumors, as alternating magnetic fields (~kHz-MHz) applied to such MNPs may result in the generation of heat, thus functioning as hyperthermia agents. Accordingly, by conjugating MNPs to the instant tumor-targeting NIR dye, selective accumulation of MNPs in tumor cells may be significantly improved for both MM diagnosis and hyperthermia therapy, whereby concerning the latter, the instant conjugate can target MNPs to tumor cells and subsequently convert electromagnetic radiation into heat to kill the tumor cells.

As but one illustrative example, a particular embodiment of an IONP conjugated to an NIR dye which may be useful with the instant invention can be synthesized according to Scheme V below, whereby this synthesis includes a symmetrical IONP-NIR dye conjugate. The IONP can be coated with a variety of linkers which may vary in length and thickness, depending upon the desired characteristics of the conjugate. As to particular embodiments, the IONP can have a diameter in a range of about 10 nanometers to about 35 nanometers. As but a first illustrative example, the IONP can have a diameter of about 15 nanometers. As but a second illustrative example, the IONP can have a diameter of about 20 nanometers. As but a third illustrative example, the IONP can have a diameter of about 30 nanometers.

Scheme V

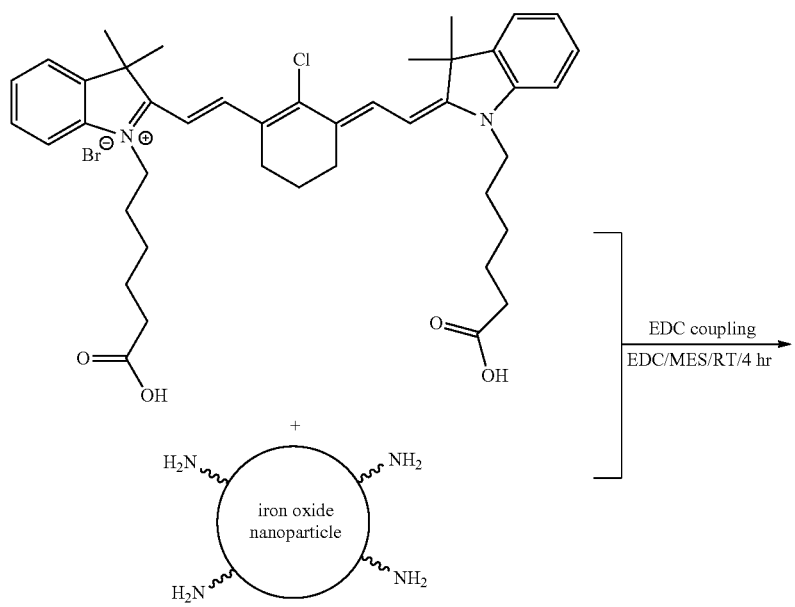

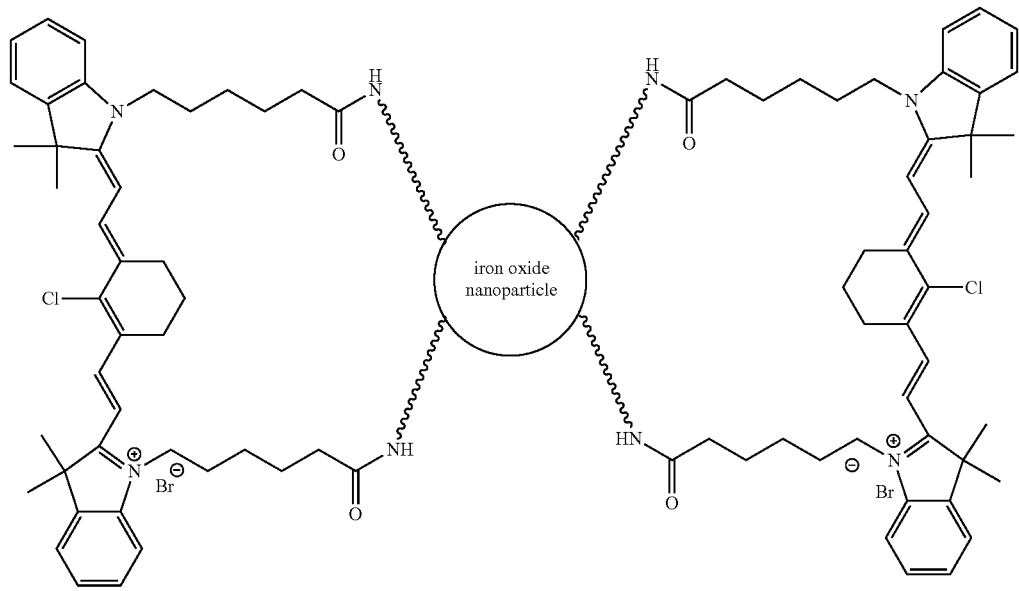

As but another illustrative example, a particular embodiment of an IONP conjugated to an NIR dye which may be useful with the instant invention can be synthesized according to Scheme VI below, whereby this synthesis includes an asymmetrical IONP-NIR dye conjugate. The IONP can be coated with a variety of linkers which may vary in length and thickness, depending upon the desired characteristics of the conjugate. As to particular embodiments, the IONP can have a diameter in a range of about 10 nanometers to about 35 nanometers. As but a first illustrative example, the IONP can have a diameter of about 15 nanometers. As but a second illustrative example, the IONP can have a diameter of about 20 nanometers. As but a third illustrative example, the IONP can have a diameter of about 30 nanometers.

Scheme VI

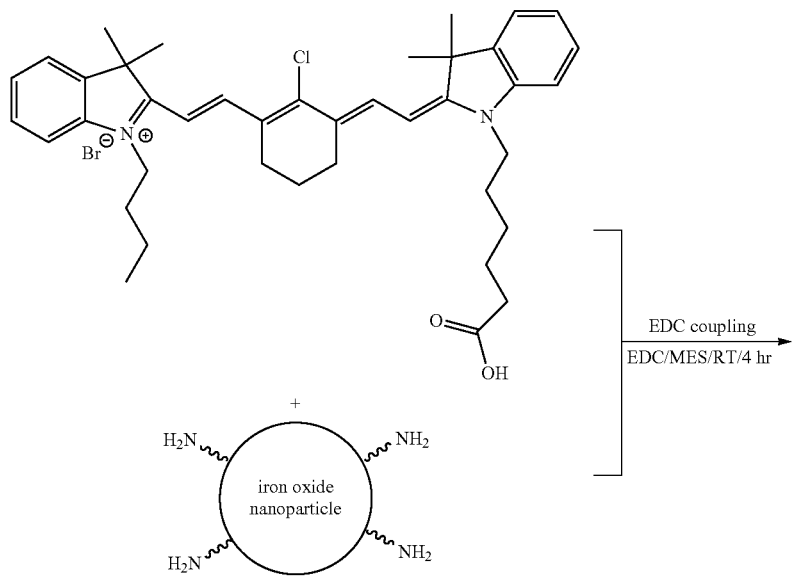

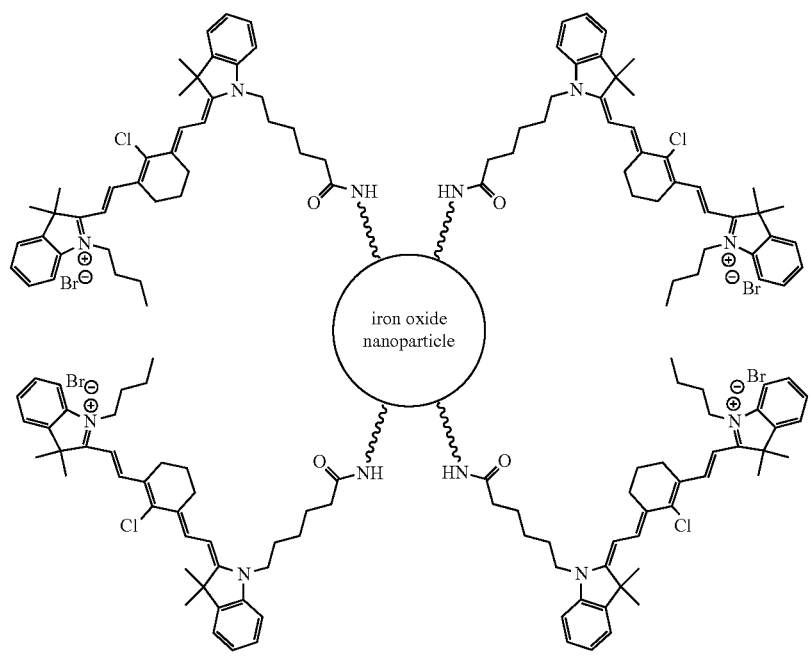

As but another illustrative example, a particular embodiment of an IONP conjugated to an NIR dye which may be useful with the instant invention can be synthesized according to Scheme VII below, whereby the IONP is linked to the NIR dye via the central ring. The IONP can be coated with a variety of linkers which may vary in length and thickness, depending upon the desired characteristics of the conjugate.

As to particular embodiments, the IONP can have a diameter in a range of about 10 nanometers to about 35 nanometers. As but a first illustrative example, the IONP can have a diameter of about 15 nanometers. As but a second illustrative example, the IONP can have a diameter of about 20 nanometers. As but a third illustrative example, the IONP can have a diameter of about 30 nanometers.

Scheme VII
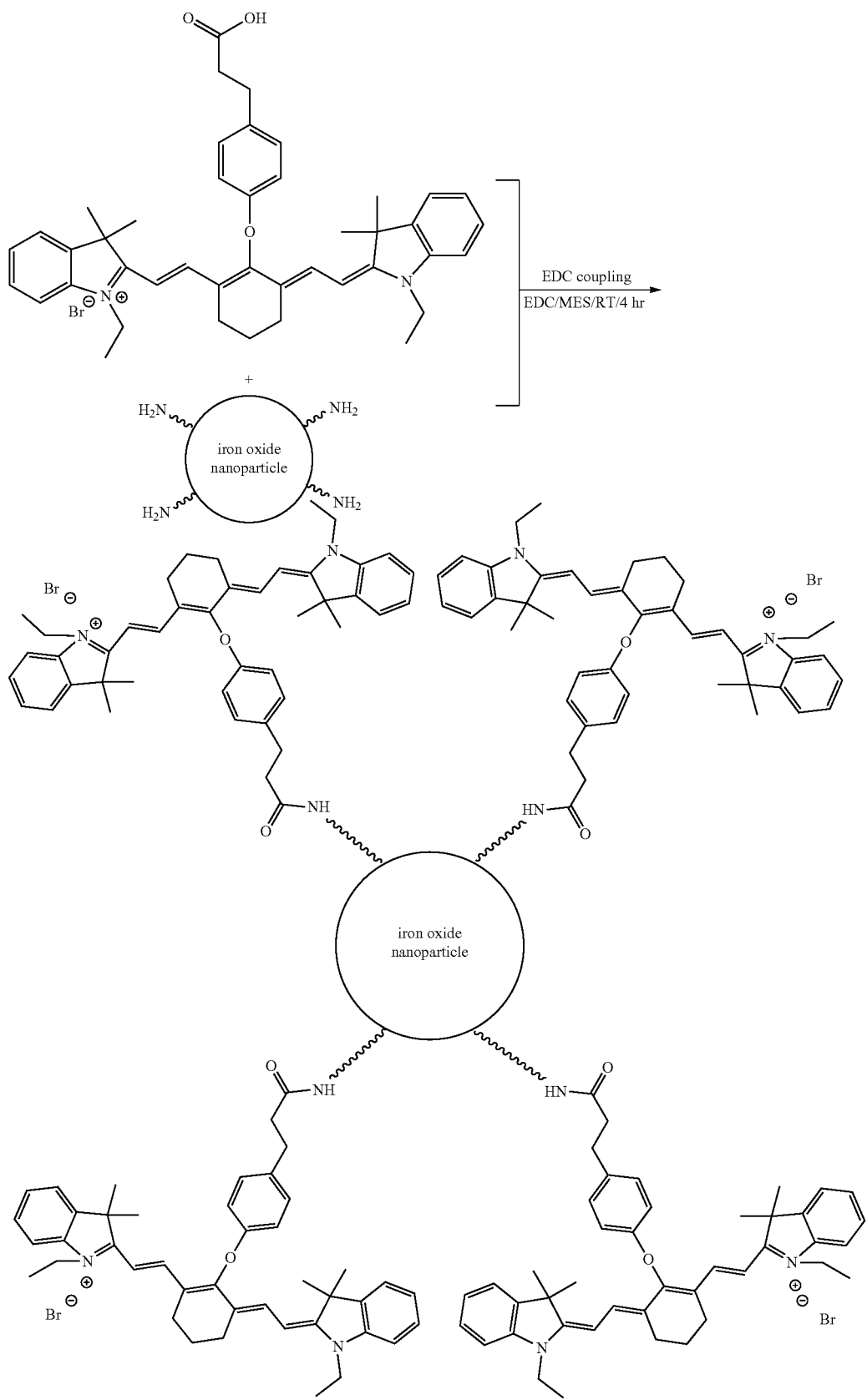

As but another illustrative example, a particular embodiment of an IONP conjugated to an NIR dye which may be useful with the instant invention can be synthesized according to Scheme VIII below, whereby the IONP-NIR dye conjugate can be based on a carboxylate-functionalized IONP. The IONP can be coated with a variety of linkers which may vary in length and thickness, depending upon the desired characteristics of the conjugate. As to particular embodiments, the IONP can have a diameter in a range of about 10 nanometers to about 35 nanometers. As but a first illustrative example, the IONP can have a diameter of about 15 nanometers. As but a second illustrative example, the IONP can have a diameter of about 20 nanometers. As but a third illustrative example, the IONP can have a diameter of about 30 nanometers.

As but another illustrative example, a particular embodiment of an IONP conjugated to an NIR dye which may be useful with the instant invention can be synthesized according to Scheme IX below, whereby the IONP-NIR dye conjugate can be based on a mono-functionalized NIR dye and a carboxylate-functionalized IONP. The IONP can be coated with a variety of linkers which may vary in length and thickness, depending upon the desired characteristics of the conjugate. As to particular embodiments, the IONP can have a diameter in a range of about 10 nanometers to about 35 nanometers. As but a first illustrative example, the IONP can have a diameter of about 15 nanometers. As but a second illustrative example, the IONP can have a diameter of about 20 nanometers. As but a third illustrative example, the IONP can have a diameter of about 30 nanometers.

Scheme VIII

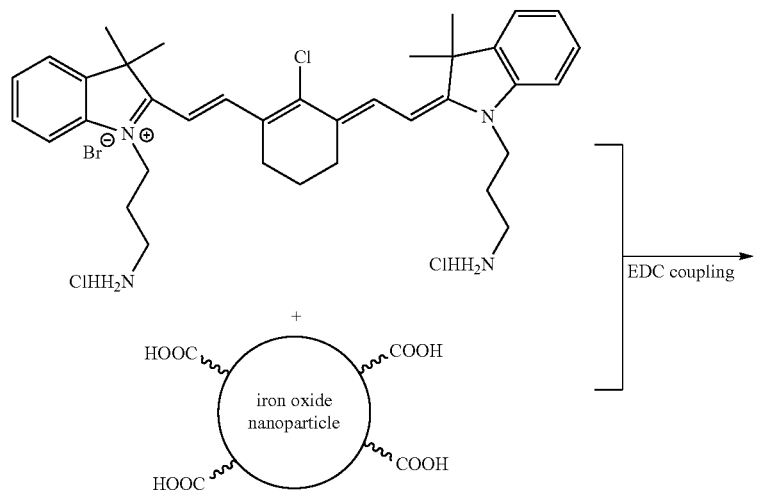

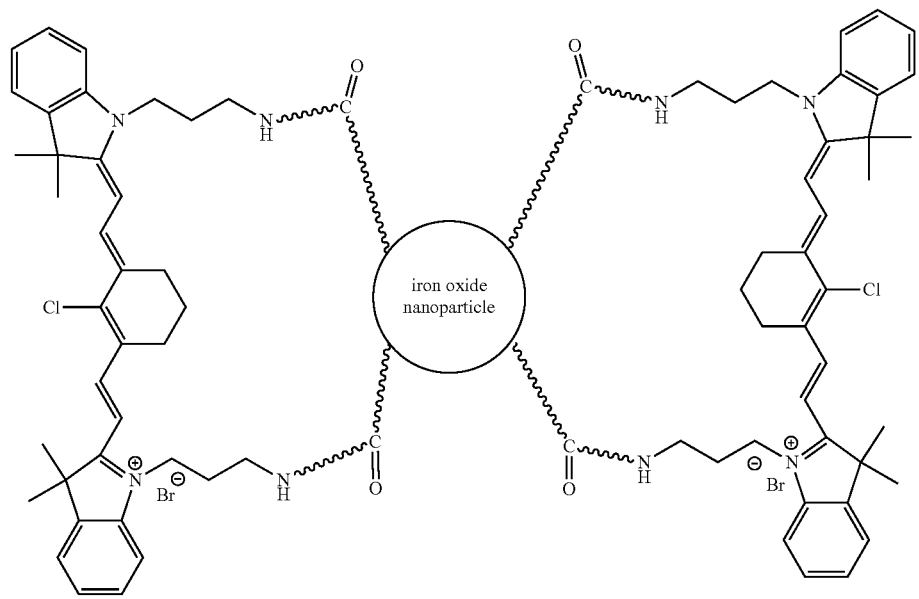

Scheme IX

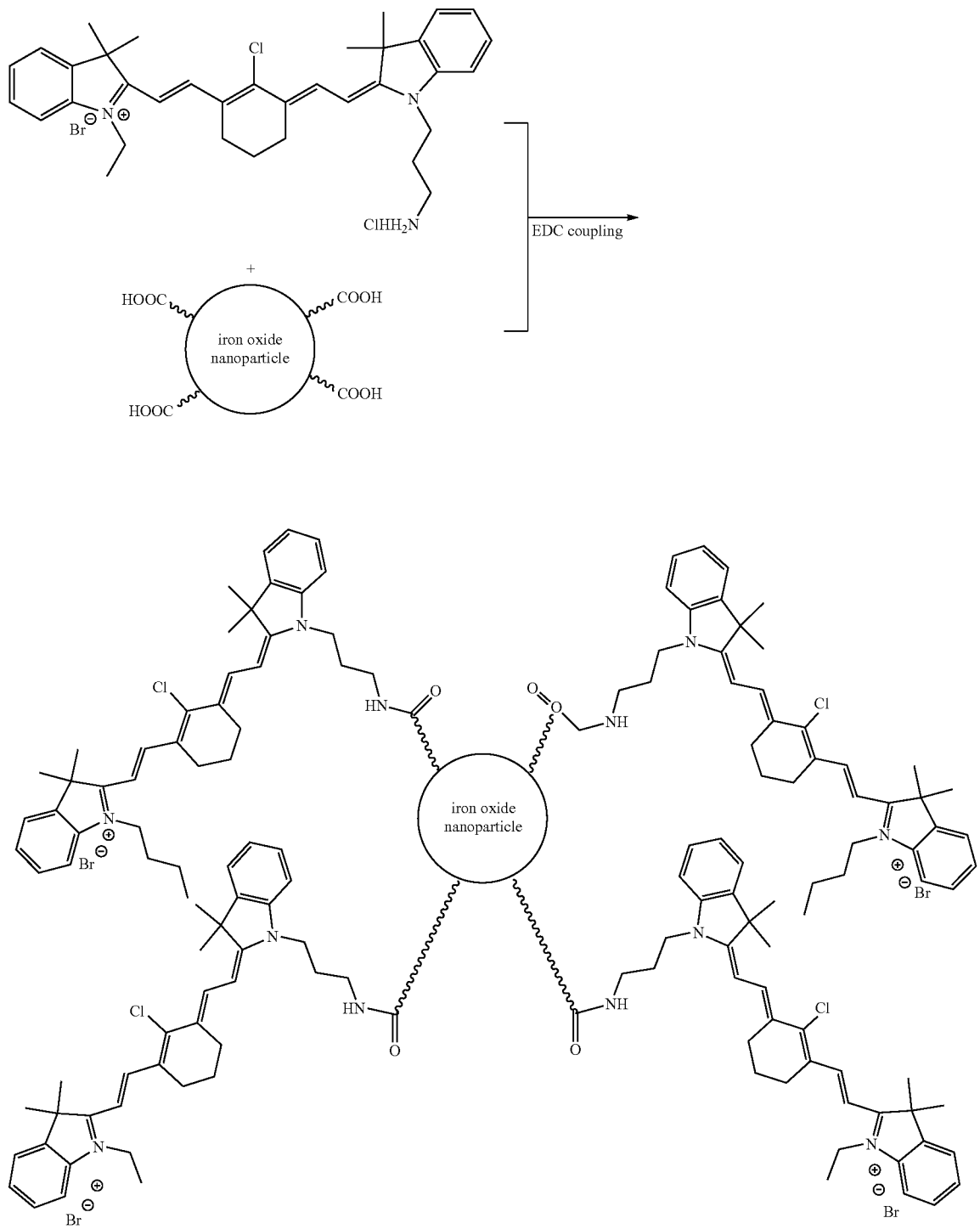

As but another illustrative example, a particular embodiment of an IONP conjugated to an NIR dye which may be useful with the instant invention can be synthesized according to Scheme X below, whereby the IONP-NIR dye conjugate can be based on a central ring-functionalized NIR dye and a carboxylate-functionalized IONP. The IONP can be coated with a variety of linkers which may vary in length and thickness, depending upon the desired characteristics of the conjugate. As to particular embodiments, the IONP can have a diameter in a range of about 10 nanometers to about 35 nanometers. As but a first illustrative example, the IONP can have a diameter of about 15 nanometers. As but a second illustrative example, the IONP can have a diameter of about 20 nanometers. As but a third illustrative example, the IONP can have a diameter of about 30 nanometers.

Scheme X

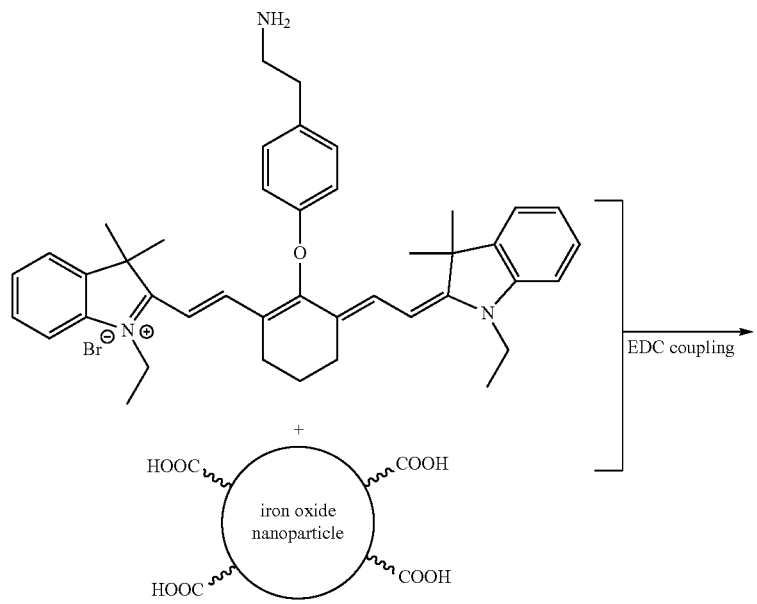

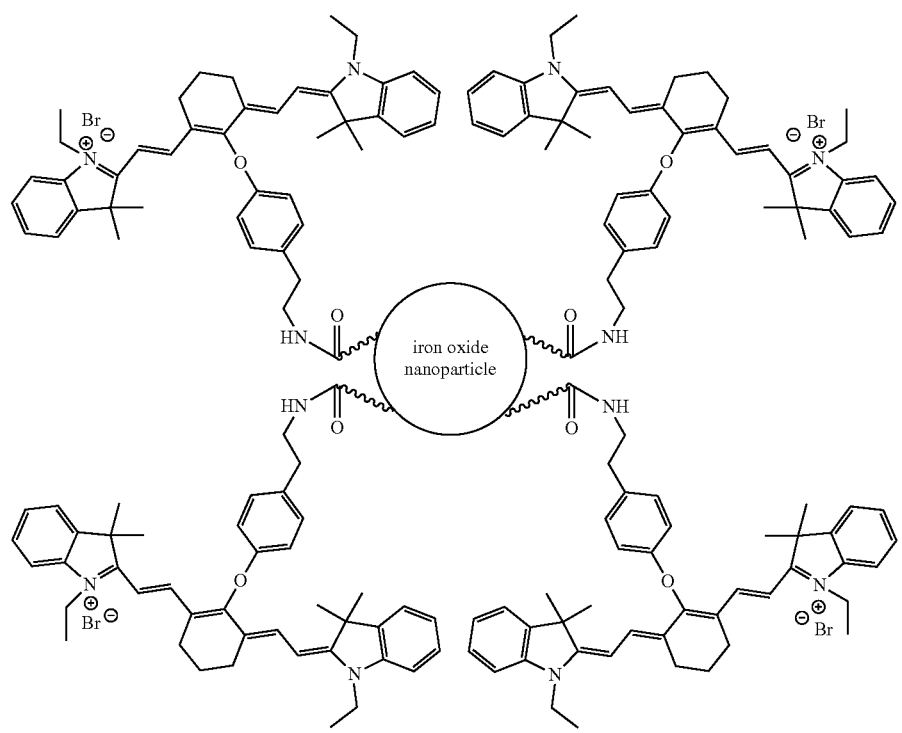

As to particular embodiments, a silica shell can surround the IONP core, which may allow control of the thickness of the linker between the IONP core and the NIR dye, the overall size of the conjugate, and/or the hydrophilicity/hydrophobicity of the conjugate (which may affect biocompatibility), whereby the NIR dye can be incorporated onto or bound to the silica shell surrounding the IONP core.

As but one illustrative example, a silica shell with amino-functionalized groups attached to its surface can be formed around the IONP core. The NIR dye can then be covalently linked, for example via an EDC coupling reaction, to the silica shell via the amino-functionalized groups to form the IONP-NIR dye conjugate, as shown in Scheme XI below.

Scheme XI
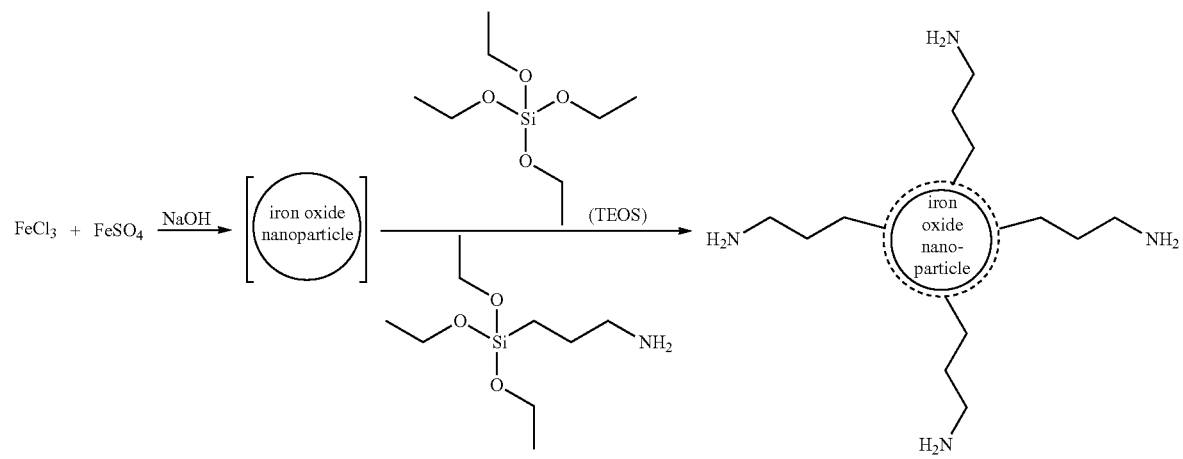
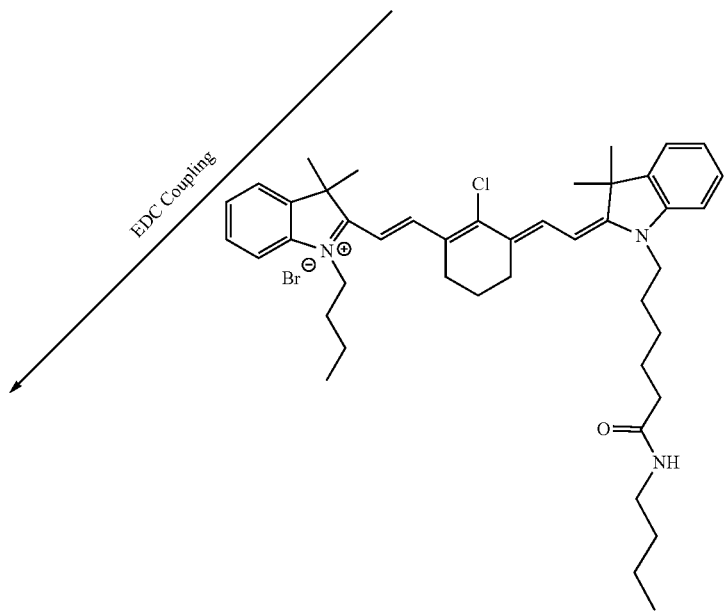

-continued
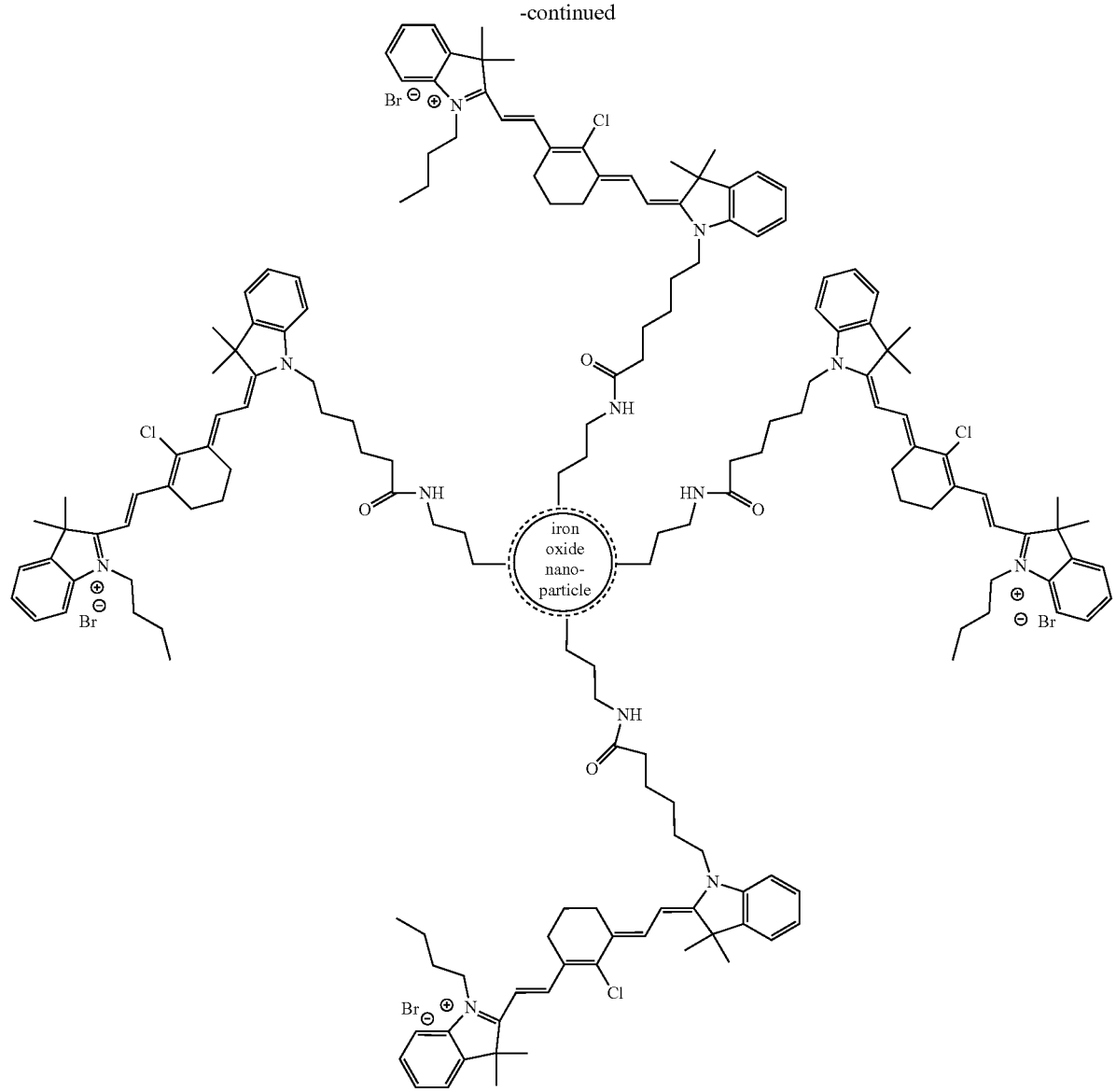
As but a second illustrative example, a conjugate including an NIR dye covalently linked to a silica shell formed about an IONP can be synthesized according to Scheme XII below, which may include only a single step:
Scheme XII
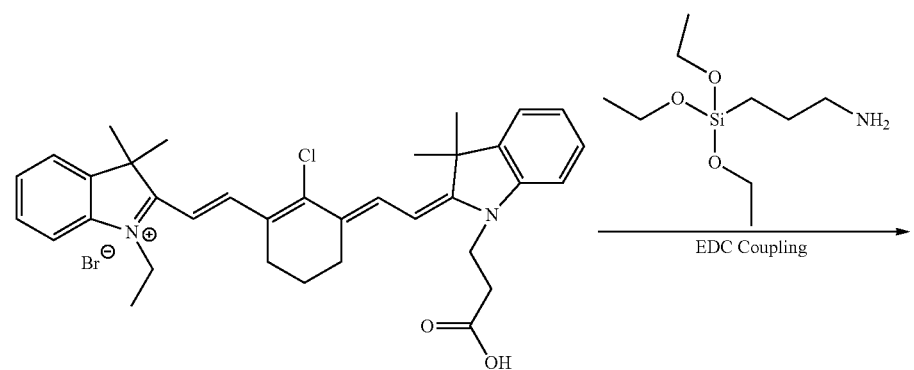

-continued
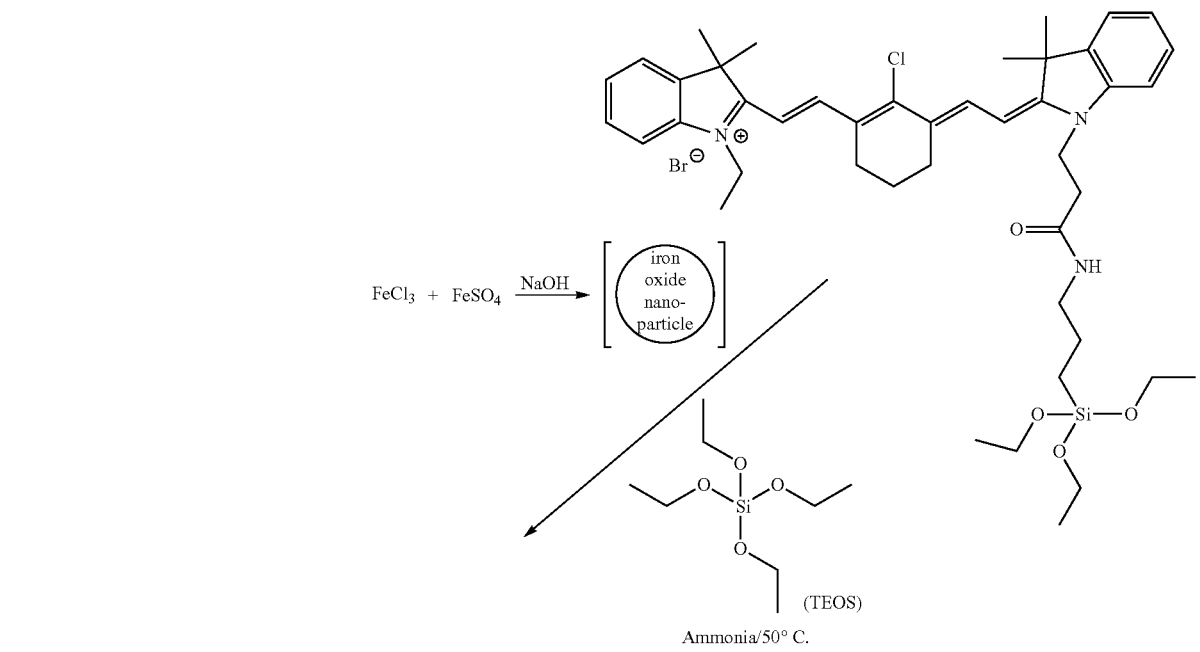
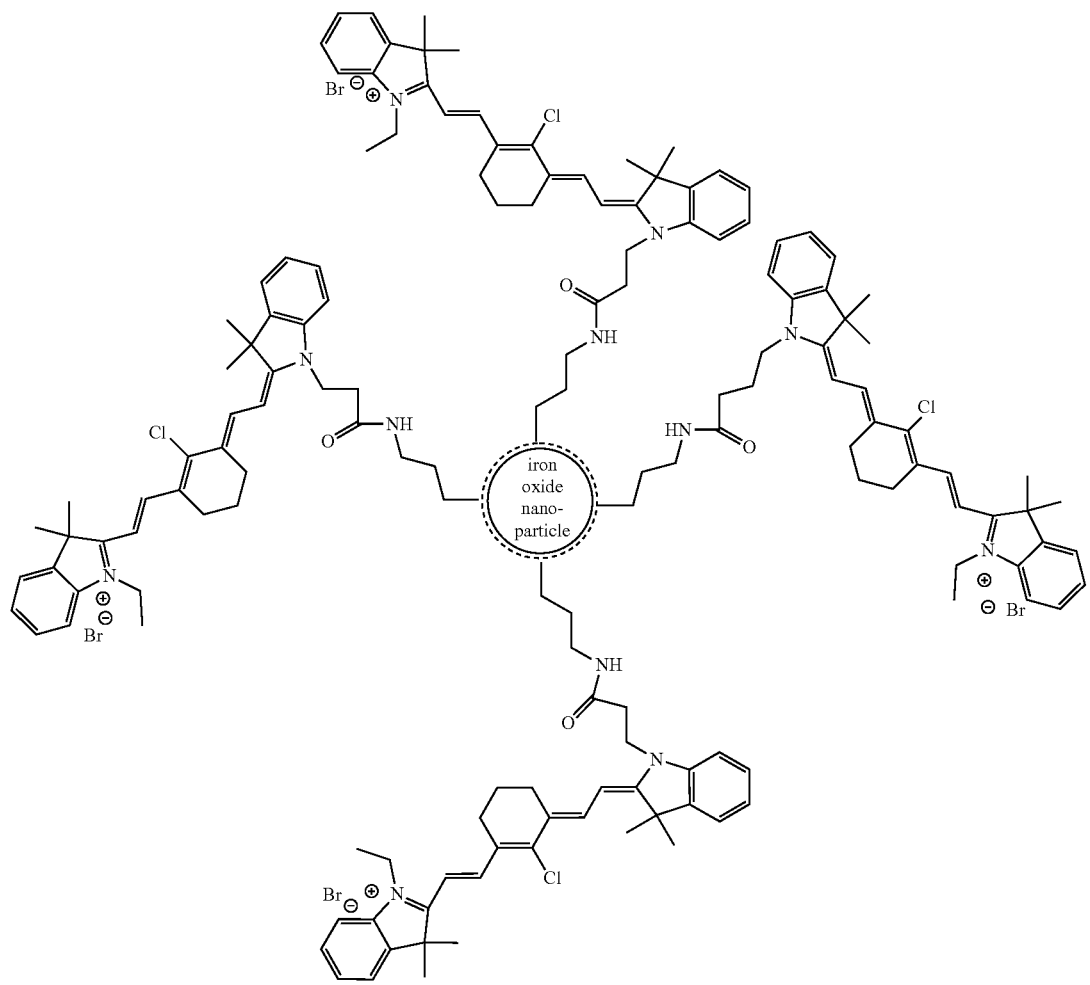

Figure 4:
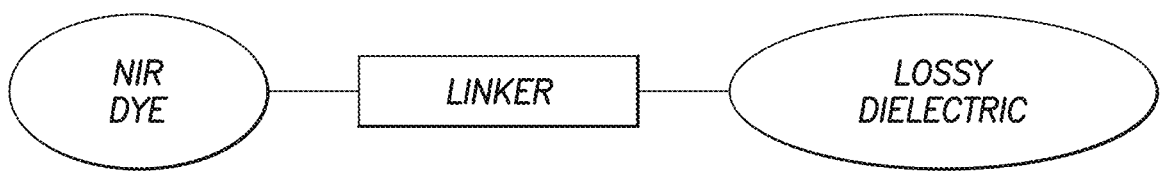
FIG. 4 is an illustration of a particular embodiment of a conjugate contemplated by the instant invention.

In a similar fashion, a conjugate including an NIR dye covalently linked to a silica shell formed about a gold nanoparticle can be synthesized according to Scheme XIII below:

Now referring primarily to FIG. 4, as another illustrative example, carbon nanoparticles, such as carbon nanospheres, carbon nanoshells, carbon nanotubes, other so-called "lossy dielectric" materials, or the like, which can function as

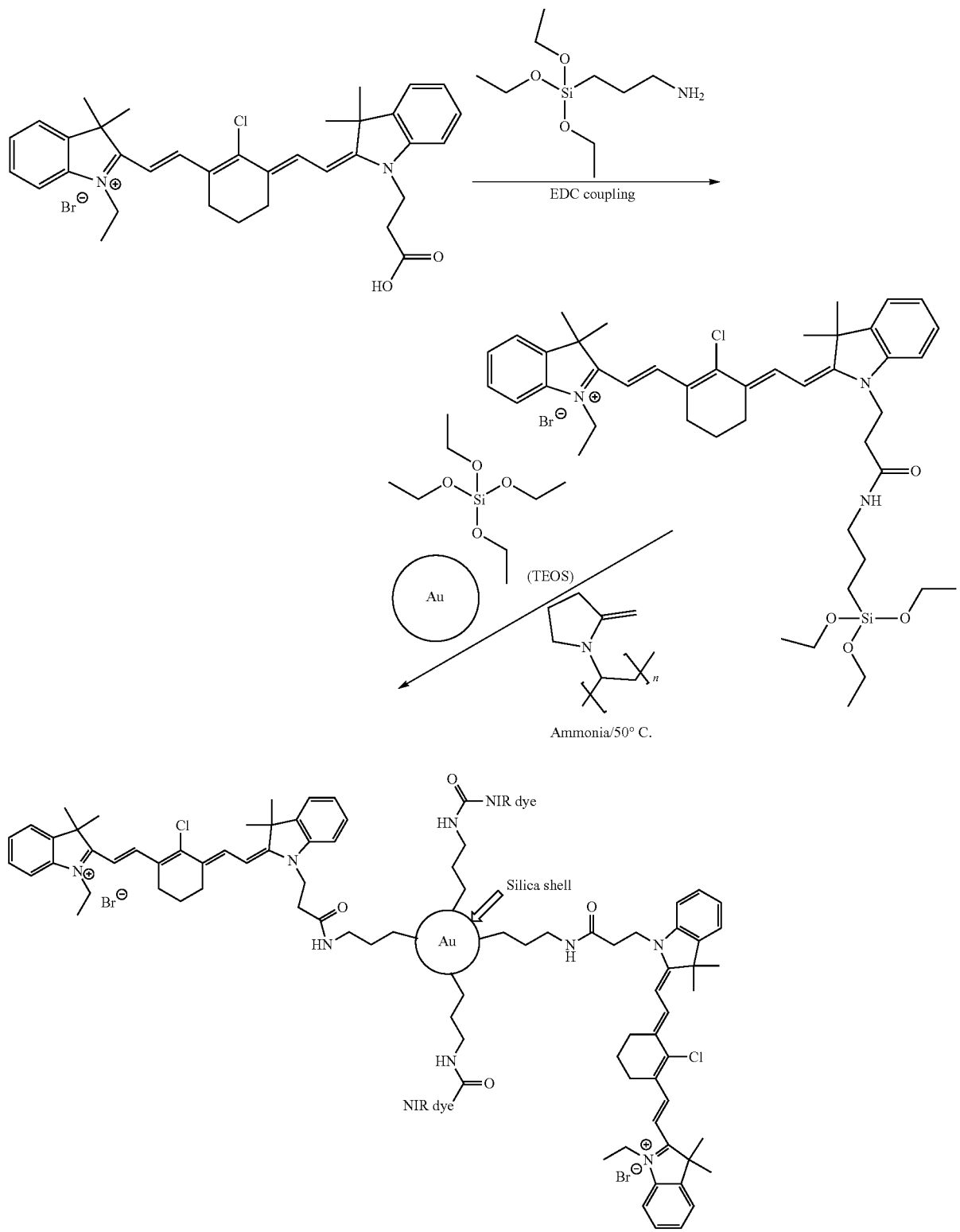

hyperthermia agents, may be useful as a therapeutic agent when conjugated to an NIR dye which can target the carbon nanoparticle-NIR dye conjugate to tumor cells, as per the instant invention.

When electric current flows through a material, some of the energy can be converted to heat (the energy can then be lost from the electromagnetic wave or current). Correspondingly, materials with medium-range conductivities may be referred to as lossy materials or lossy dielectrics, whereby an example of a lossy material with a mid-range value for conductivity is carbon.

Single walled carbon nanotubes (SWNTs) can have a wide dynamic range of electromagnetic absorption resulting from their one-dimensional structure, typically comprising a honeycomb pattern of carbon rolled into a seamless cylinder. When SWNTs are exposed to electromagnetic radiation, they can release a significant amount of heat which may be sufficient to treat or kill tumor cells. As to particular embodiments, the thermal properties of SWNTs under electromagnetic radiation may be useful to treat deep tissue tumors.

Of note, carbon nanotubes can be targeted to specific cells either through direct covalent functionalization to a targeting moiety (such as an NIR dye), or through non-covalent wrapping of a targeting moiety (such as an NIR dye).

Figure 5:
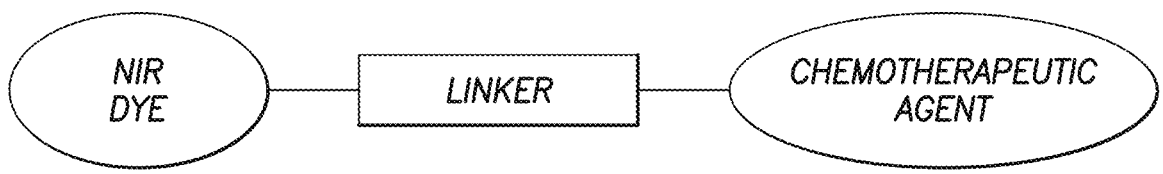
FIG. 5 is an illustration of a particular embodiment of a conjugate contemplated by the instant invention.

Now referring primarily to FIG. 5, as another illustrative example, chemotherapeutics may be useful as a therapeutic agent when conjugated to an NIR dye which can target the chemotherapeutic-NIR dye conjugate to tumor cells, as per the instant invention. For example, a few conventional chemotherapeutics which may be conjugated to an NIR dye, as per the instant invention, can include actinomycin, all-trans retinoic acid, azacitidine, azathioprine, bleomycin, bortezomib, carboplatin, capecitabine, cisplatin, chlorambucil, cyclophosphamide, cytarabine, daunorubicin, doxifluridine, doxorubicin, epirubicin, epothilone, etoposide, fluorouracil, gemcitabine, hydroxyurea, idarubicin, imatinib, irinotecan, mechlorethamine, methotrexate, mitoxantrone, nitrogen mustard, oxaliplatin, paclitaxel, pemetrexed, teniposide, tioguanine, topotecan, valrubicin, vemurafenib, vinblastine, vincristine, and vindesine.

As but one illustrative example, a particular embodiment of a chemotherapeutic, namely doxorubicin (DOX), conjugated to an NIR dye which may be useful with the instant invention can be synthesized according to Scheme XIV below. DOX is a commonly used clinical anticancer agent; however, like most traditional chemotherapeutics, DOX can be non-specific and thus, DOX can be toxic to normal cells, especially those of the heart, liver, and kidneys. Following, it is herein contemplated that the adverse side effects of DOX may be reduced, minimized, or eliminated by the present invention which targets DOX via the instant NIR dye to the tumor site/tumor cells. Of note, in the below example, the acid-labile hydrazine bond may be cleaved once the DOX-NIR dye conjugate enters a tumor site or tumor cell, which may be acidic, thus releasing DOX at the targeted location.

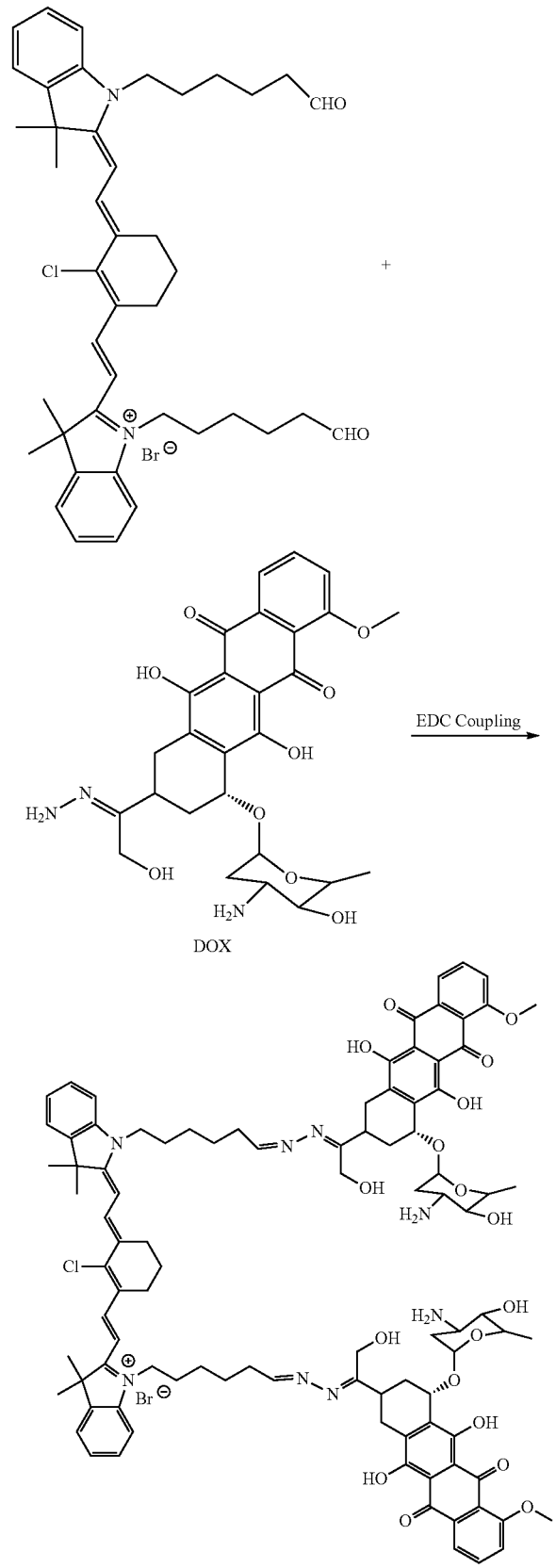

Scheme XIV

Additionally, other conjugates including DOX linked to an NIR dye which may be useful with the instant invention are shown in Formulas IV and V, as follows:

IV

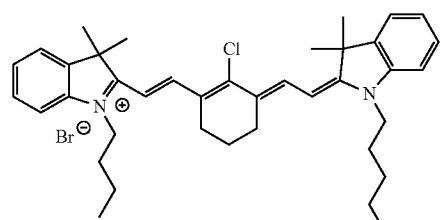

V

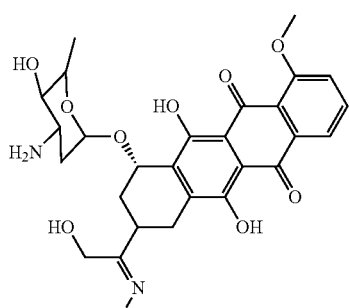

Figure 6:
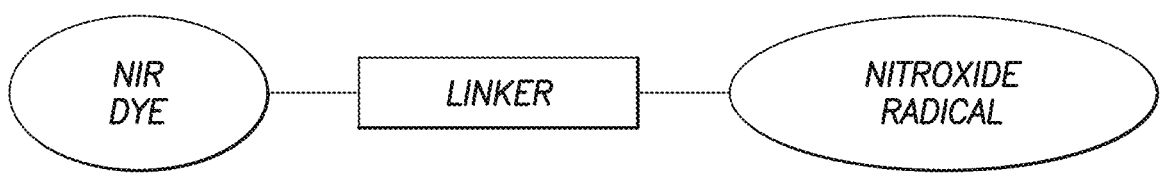
FIG. 6 is an illustration of a particular embodiment of a conjugate contemplated by the instant invention.

Now referring primarily to FIG. 6, as another illustrative example, a nitroxide radical may be useful as a therapeutic agent when conjugated to an NIR dye which can target the nitroxide radical-NIR dye conjugate to tumor cells, as per the instant invention.

As cancer cells may produce higher levels of free radicals than normal cells due to their active metabolism associated with the dysregulation of various cellular events, these cells can be under constant oxidative stress. While an overproduction of high levels of free radicals can result in detrimental cell damage and ultimately cell death, moderate levels may facilitate cancer cell survival and promote tumor growth. Following, cancer cells may rely heavily on antioxidant enzymes and other adaptive antioxidant defenses to maintain intracellular levels of reactive oxidative species (ROS) within a tolerable threshold and thus protect these cells from damage.

Correspondingly, nitroxide radicals may be suitable cancer therapeutics, as these compounds, either alone or when combined with another therapy (such as a chemotherapeutic), can intensify the oxidative stress in cancer cells, which can lead to cell death.

Exemplary conjugates including nitroxide radicals bound to an NIR dye which may be useful with the instant invention are shown in Formulas VI, VII, and VIII, as follows:

VI

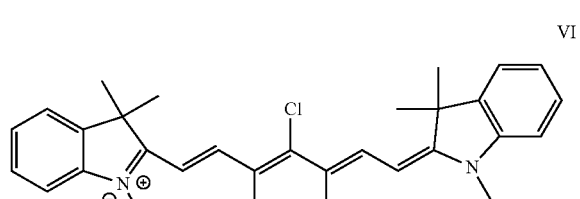

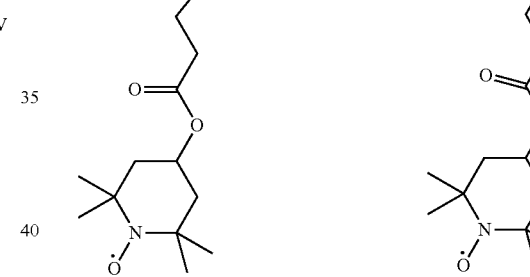

VII

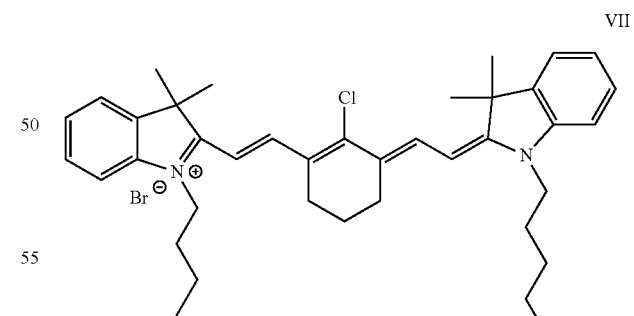

VIII

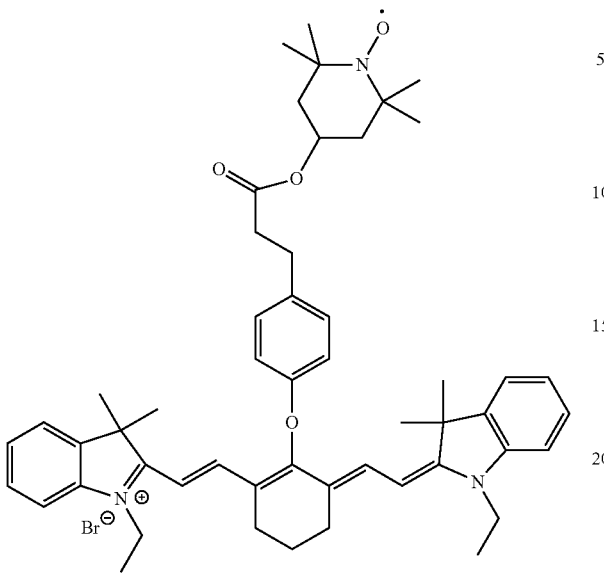

Figure 7:
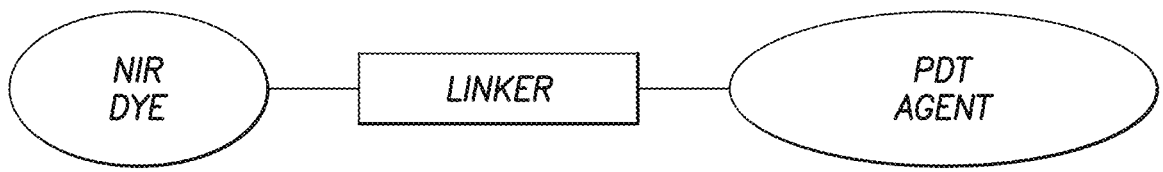
FIG. 7 is an illustration of a particular embodiment of a conjugate contemplated by the instant invention.

Now referring primarily to FIG. 7, as another illustrative example, a photodynamic therapy (PDT) agent may be useful as a therapeutic agent when conjugated to an NIR dye which can target the PDT agent-NIR dye conjugate to tumor cells, as per the instant invention. Generally, PDT includes administration of a photosensitizer, for example via injection into the bloodstream or application to an affected area of skin. Upon activation of the photosensitizer by light, one or more processes may be initiated which can result in tumor cell death. However, accumulation of conventional photosensitizers in tumor cells can be low, whereby an example of one such PDT agent can be chlorin-e6 PSs. It is herein contemplated that the instant invention can increase accumulation of PDT agents in tumor cells.

Exemplary conjugates including a PDT agent bound to an NIR dye which may be useful with the instant invention are shown in Formulas IX, X, and XI, as follows:

IX

X, XI

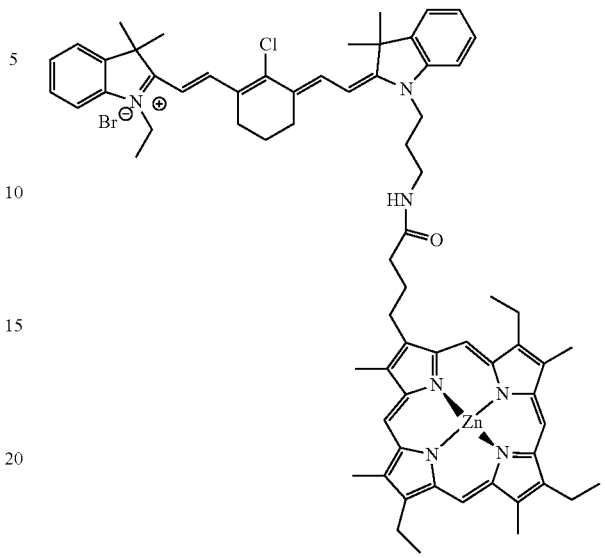

Figure 8:
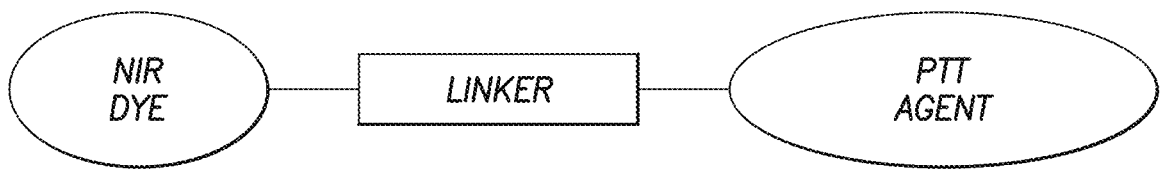
FIG. 8 is an illustration of a particular embodiment of a conjugate contemplated by the instant invention.

Now referring primarily to FIG. 8, as another illustrative example, a photothermal therapy (PTT) agent may be useful as a therapeutic agent when conjugated to an NIR dye which can target the PTT agent-NIR dye conjugate to tumor cells, as per the instant invention. One such PTT agent may be gold nanoparticles.

Linker

Linkers useful with the instant invention can be heterobifunctional, thus reacting with both the NIR dye and the therapeutic or diagnostic agent to form a conjugate, whereby as illustrative examples, the linker may be a polyethylene glycol (PEG), a polymer, a peptide, DNA, a silica nanoparticle, or the like.

The particular linker used to covalently attach the instant tumor-targeting NIR dye and a therapeutic or diagnostic agent can have a profound impact on the conjugate's efficacy. Firstly, the hydrophobicity and/or hydrophilicity of the linker can influence the conjugate's biocompatibility and circulation time. Secondly, the length, thickness, flexibility, and rigidity of the linker can influence NIR fluorescence, and correspondingly detection of tumor cells.

As to particular embodiments, a relatively rigid linker may be preferable, and can be configured as a shell structure like iron-oxide or silica.

As to other particular embodiments, a relatively flexible linker may be preferable, and can be formed from a biocompatible PEG, which may have various lengths. PEGylation may be useful to extend the conjugate's time in circulation, which may be beneficial as it is postulated that conjugates with longer blood circulation times have a higher probability of delivery to the tumor site.

As to particular embodiments, some therapeutic or diagnostic agents need to be free from other parts of the conjugate in order to be effective. Hence, linkers which can "self-destruct" following entrance into the tumor cell can be advantageous. For example, particular linkers can be cleaved by enzymes, nucleophilic reagents, reducing/oxidizing agents, photo-irradiation, or an acidic environment, depending on the nature of the bonds. Conjugates including these activatable/cleavable linkers can be formulated to exploit the differences between tumor cells and normal cells, such as differences in specific enzymes and/or pH.

As stated above, as to particular embodiments, heterobifunctional linkers may be useful for the instant invention and, as but one illustrative example, for conjugates including an IONP, whereby one end of the linker can have a functional group with high affinity for the IONP, such as a phosphonic acid, a carboxylate, a silica nanoshell, a gold nanoshell, a catechol, or a bifunctional polymer. The other end of the linker can have a functional group with high affinity for the NIR dye, such as an amino group, a carboxylate, an alcohol, an azide, or an acetylene group.

As but one illustrative example, a particular embodiment of a heterobiofunctional PEG linker which may be useful with the instant invention can be synthesized according to Scheme XV below:

Scheme XV

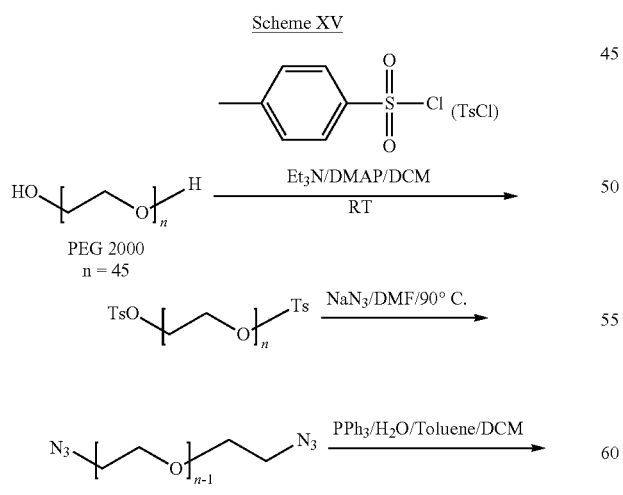

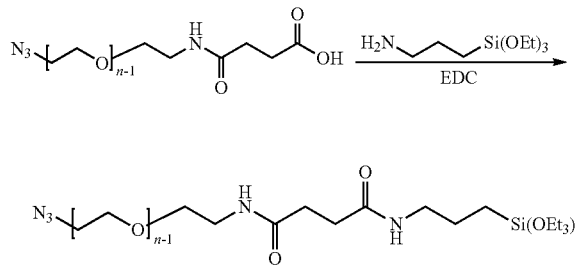

Exemplary linkers which may be useful with the instant invention are shown in Formulas XII, XIII, XIV, and XV, as follows, whereby illustrative examples of particular embodiments of n can be 3, 5, 8, 12, 22, 45, or 113.

XII

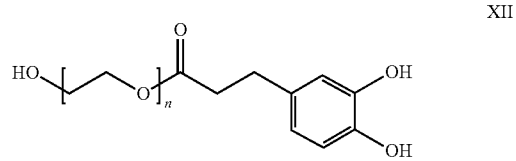

XIII

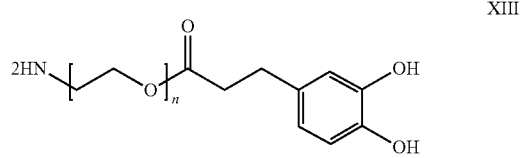

XIV

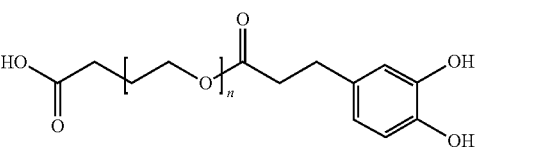

XV

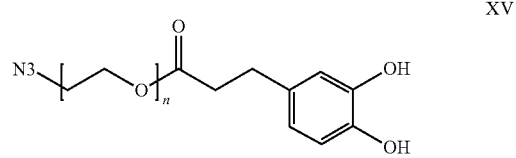

Example 1

As an example, a particular embodiment of an IONP-NIR dye conjugate, termed Conjugate I, which may be useful with the instant invention is shown in Formula XVI, as follows, whereby the IONP can have a diameter of about 30 nanometers:

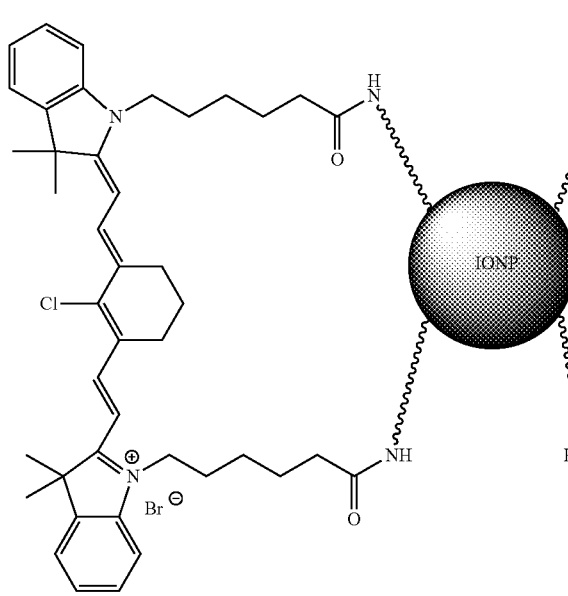
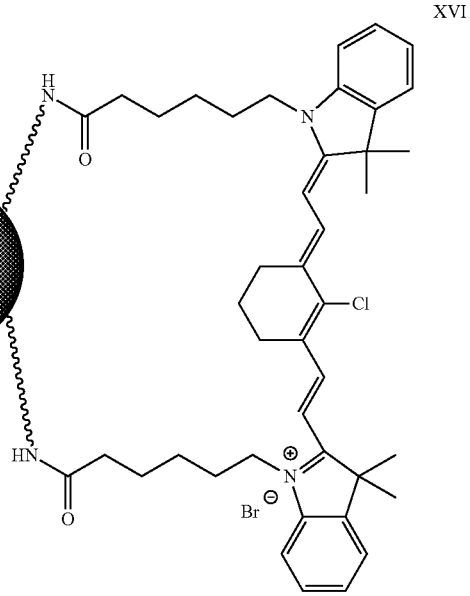

XVI

Figure 9:
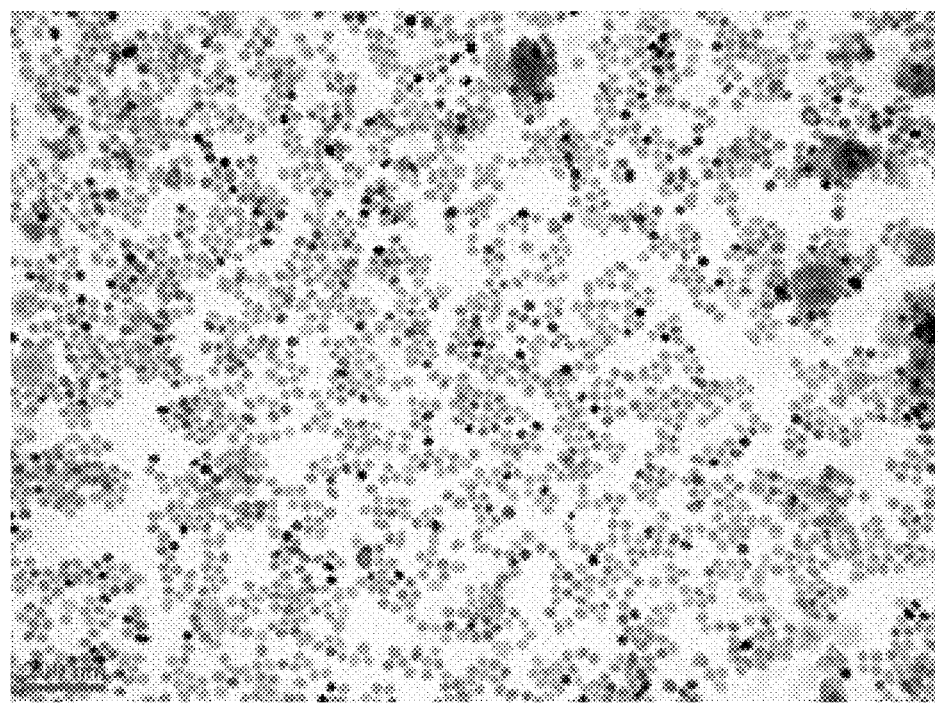
FIG. 9 shows a transmission electron microscope (TEM) image of Conjugate I.

Now referring primarily to FIG. 9, a transmission electron microscope (TEM) image of Conjugate I is shown.

Figure 10:
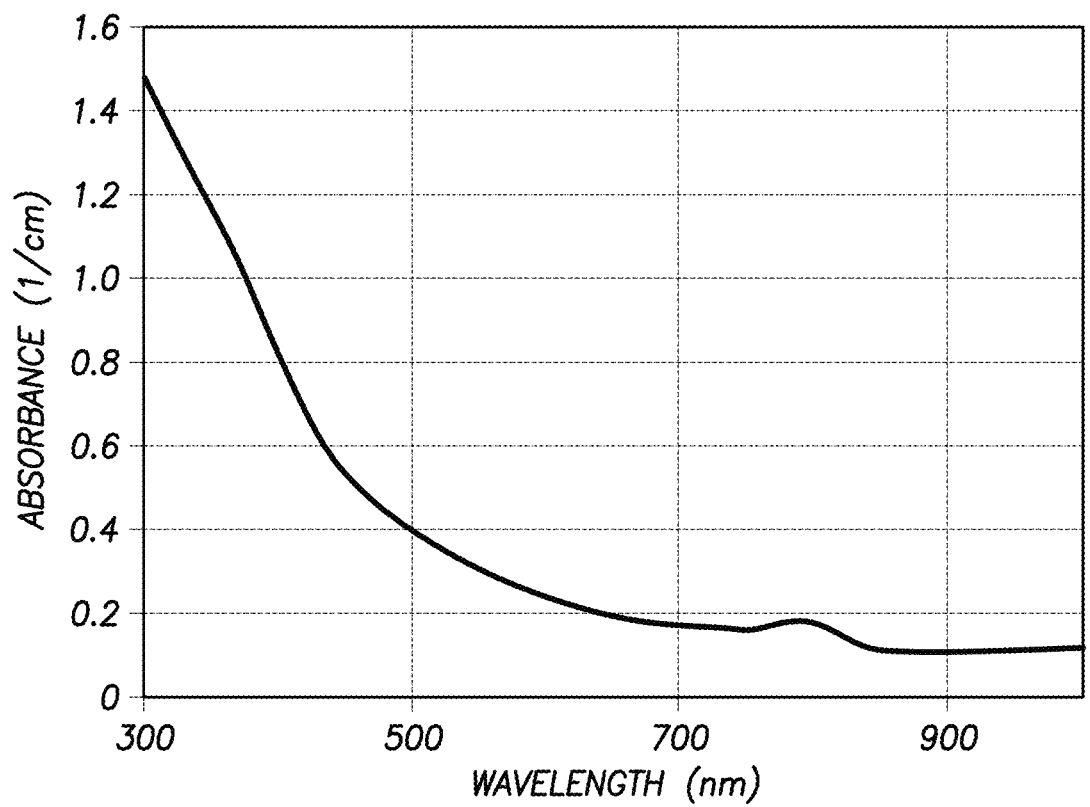
FIG. 10 shows a UV-visible spectroscopy graph including an IONP curve and NIR peak.

Now referring primarily to FIG. 10, a UV-visible spectroscopy graph including an IONP curve and NIR peak at 790 nanometers is shown.

Figure 11:
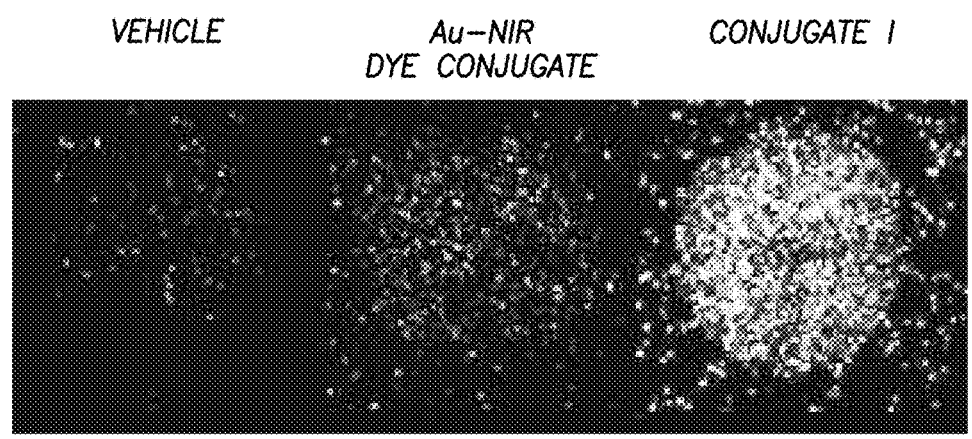
FIG. 11 shows uptake of (i) Conjugate I, (ii) a Au-NIR dye conjugate, and (iii) vehicle in colon cancer SW620 organoids via IR imaging.

Now referring primarily to FIG. 11, uptake of (i) Conjugate I, (ii) a Au-NIR dye conjugate, and (iii) vehicle in colon cancer SW620 organoids is shown via IR imaging, whereby the uptake of Conjugate I is greater than the uptake of the Au-NIR dye conjugate as well as the vehicle.

Figure 12:
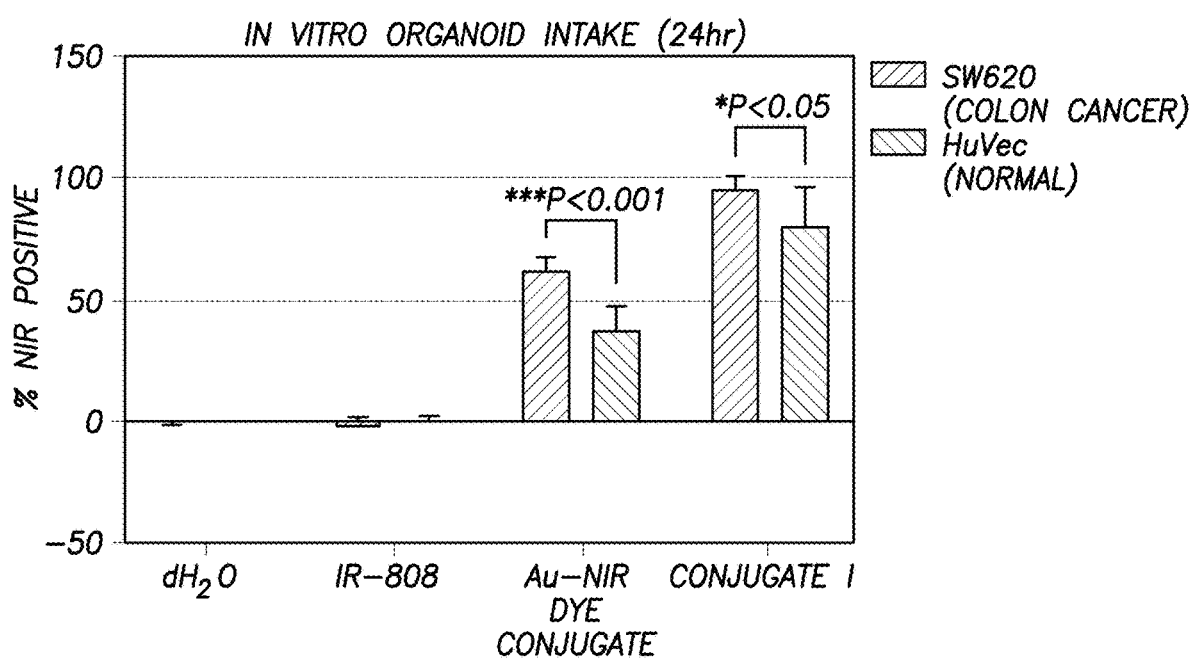
FIG. 12 shows a graph of the uptake of (i) Conjugate I, (ii) an Au-NIR dye conjugate, (iii) IR-808, and (iv) $dH_2O$ in (a) colon cancer SW620 organoids and (b) HuVec "normal" organoids.

Now referring primarily to FIG. 12, a graph of the uptake of (i) Conjugate I, (ii) an Au-NIR dye conjugate, (iii) IR-808, and (iv) $dH_2O$ in (a) colon cancer SW620 organoids and (b) HuVec "normal" organoids after 24 hours is shown, whereby the uptake of Conjugate I is greater in the colon cancer SW620 organoid than in the HuVec "normal" organoid.

Example 2

To study the hyperthermia properties of the instant conjugates, an induction heating system can be used to generate magnetic fields from 0 to about 50 mT at frequencies from about 100 kHz to about 400 kHz, whereby the magnetic field can heat a magnetic nanoparticle, such as IONP, based upon the type of magnetic nanoparticle, the concentration of the magnetic particles, the strength of the magnetic field, and/or the frequency of the magnetic field.

Figure 13:
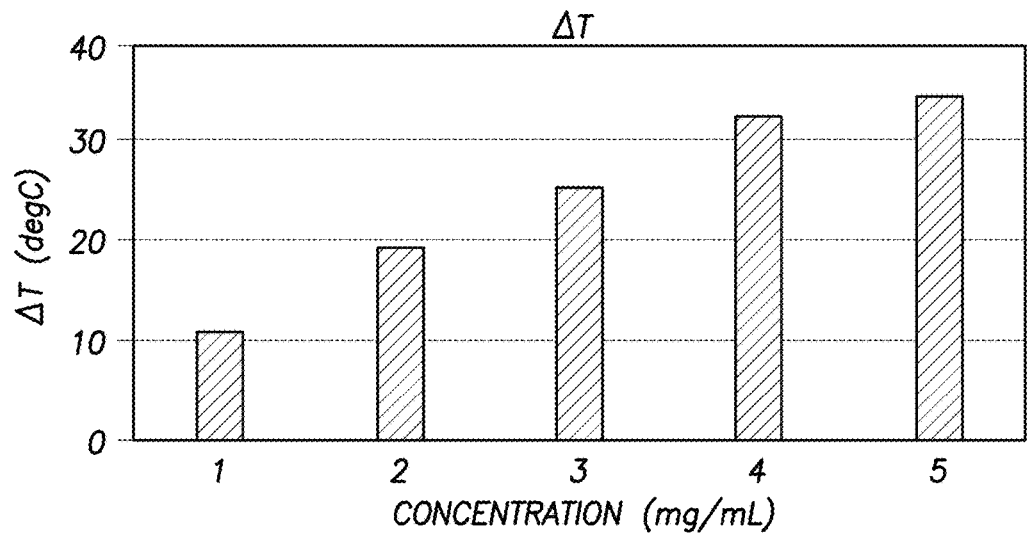
FIG. 13 shows a graph of temperature as a function of concentration of an embodiment of the instant magnetic nanoparticles.

Now referring primarily to FIG. 13, a graph of temperature as a function of concentration of the magnetic nanoparticles in a 0.5 mL test tube is shown, whereby the experimental parameters included 4.5 kW and 187 kHz. It can be seen that temperature increases as the magnetic nanoparticle concentration increases.

Figure 14:
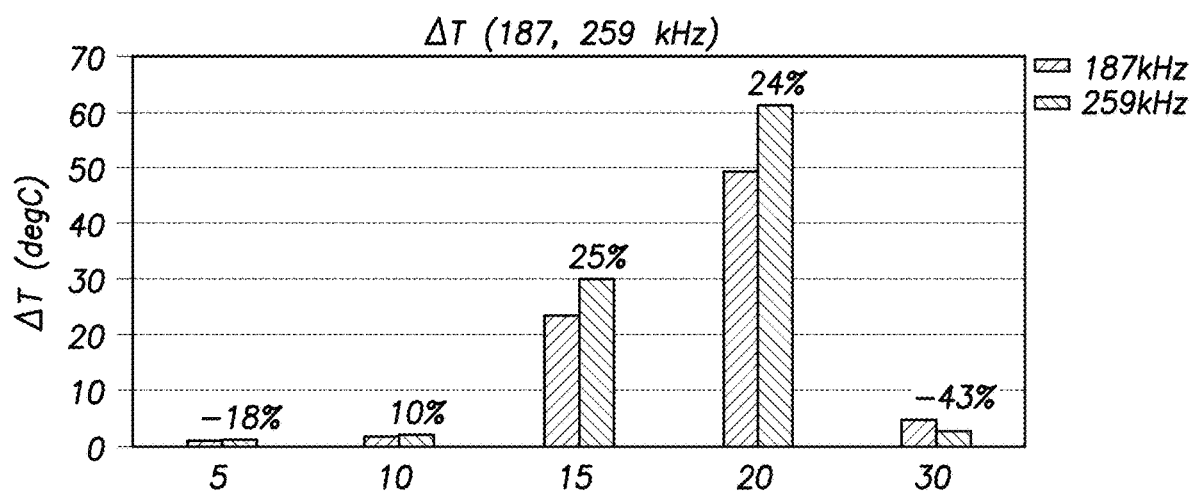
FIG. 14 shows a graph of temperature relative to two frequencies of an embodiment of the instant magnetic nanoparticles.
Figure 16:
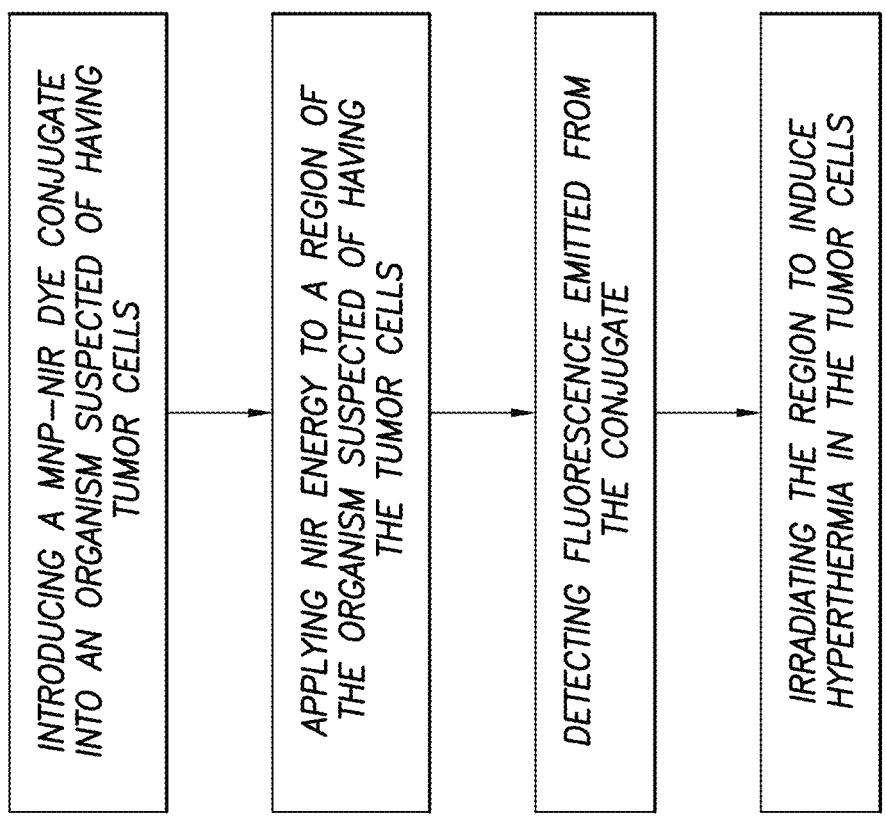
FIG. 16 shows a particular embodiment of a method of using the instant invention.
Figure 15:
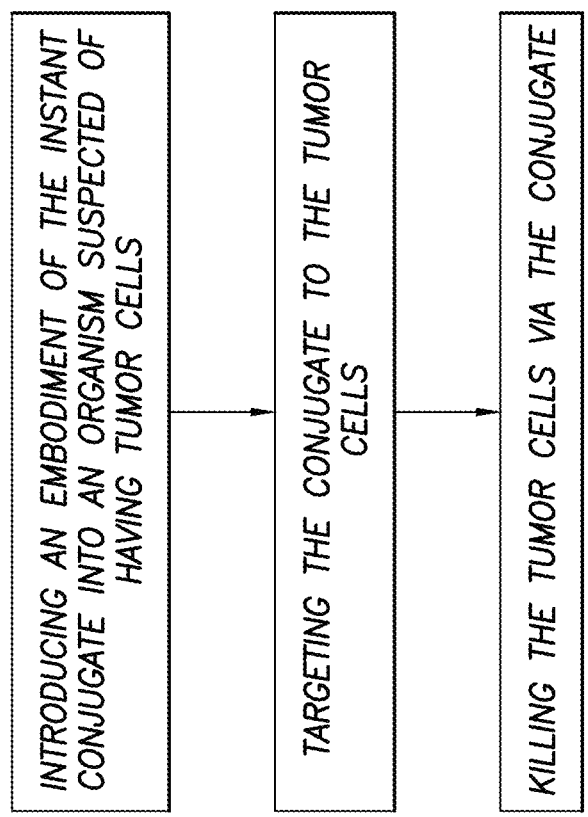
FIG. 15 shows a particular embodiment of a method of using the instant invention.
Figure 17:
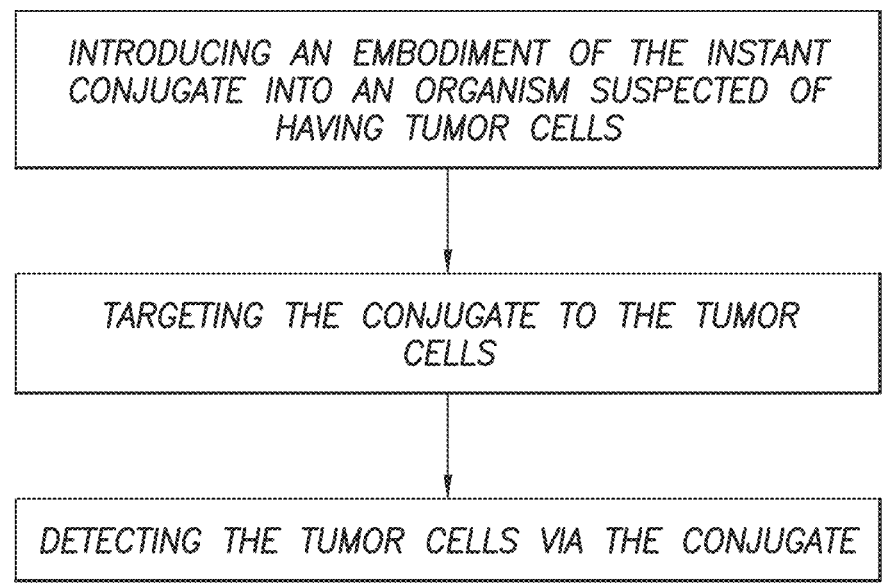
FIG. 17 shows a particular embodiment of a method of using the instant invention.

Now referring primarily to FIG. 14, a graph of temperature relative to two frequencies, namely 187 kHz and 259 kHz, is shown, whereby the experiment included exposing magnetic nanoparticles at a concentration of 5 mg/mL in a 0.5 mL test tube to the experimental parameters for 10 minutes.

Method

As to particular embodiments, the instant invention can be used in a method of killing cancer cells, whereby the method can include (i) introducing an embodiment of the instant conjugate into an organism suspected of having cancer cells, whereby the conjugate is targeted to the cancer cells, and (ii) killing the cancer cells via the conjugate.

As to particular embodiments, the instant invention can be used in a method of killing cancer cells, whereby the method can include introducing an embodiment of the instant conjugate into an organism suspected of having cancer cells, shining a NIR light on a region suspected of having the cancer cells, detecting a fluorescence from the conjugate to locate the cancer cells, and irradiating the region to induce hyperthermia in the cancer cells.

As to particular embodiments, the instant invention can be used in a method of detecting cancer cells, whereby the method can include (i) introducing an embodiment of the instant conjugate into an organism suspected of having cancer cells, whereby the conjugate is targeted to the cancer cells, and (ii) detecting the tumor cells via the conjugate.

As can be easily understood from the foregoing, the basic concepts of the present invention may be embodied in a variety of ways. The invention involves numerous and varied embodiments of NIR dyes and associated conjugates and methods for making and using such NIR dyes and associated conjugates.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "therapeutic" should be understood to encompass disclosure of the act of "providing therapy"—whether explicitly discussed or not—and, conversely, were there effectively disclosure of the act of "providing therapy", such a disclosure should be understood to encompass disclosure of an "therapeutic" and even a "means for providing therapy." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the NIR dyes and associated conjugates herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method of treating or killing tumor cells, comprising:
   administering a tumor-targeting conjugate to a subject, said conjugate comprising a heptamethine cyanine dye covalently bound to a magnetic nanoparticle via a linker;
   wherein the tumor-targeting component of said conjugate consists of said heptamethine cyanine dye; and
   inducing hyperthermia in said tumor cells via electromagnetic radiation having a frequency comprising kilohertz or megahertz;
   wherein said linker comprises one of the following compositions:

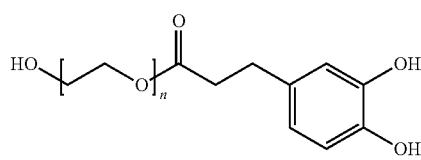

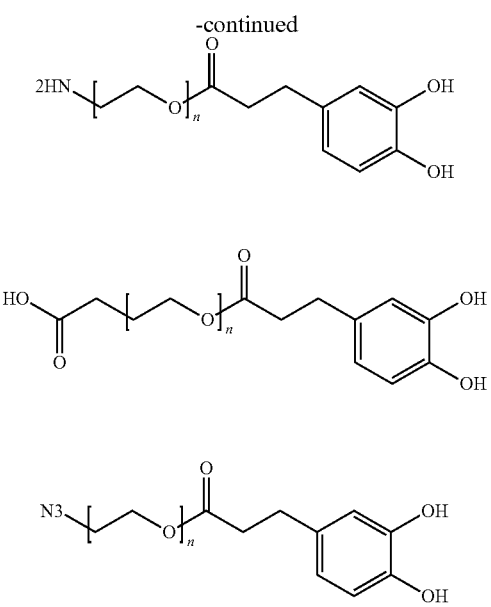

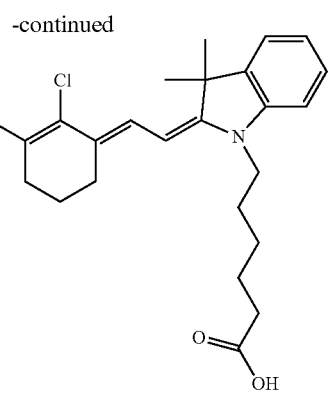

wherein n is 3, 5, 8, 12, 22, 45, or 113.

2. The method of claim 1, wherein said magnetic nanoparticle comprises iron oxide.

3. The method of claim 1, wherein said electromagnetic radiation results in the generation of heat by said magnetic nanoparticle.

4. The method of claim 1, wherein said electromagnetic radiation comprises an alternating magnetic field.

5. The method of claim 2, wherein said magnetic nanoparticle has a diameter in a range of between about 10 nanometers to about 35 nanometers.

6. The method of claim 1, wherein said magnetic nanoparticle is linked to said heptamethine cyanine dye via a central cyclohexyl ring of said heptamethine cyanine dye.

7. The method of claim 1, wherein said magnetic nanoparticle is linked to said heptamethine cyanine dye via a nitrogen of an indole moiety of said heptamethine cyanine dye.

8. The method of claim 1, wherein said linker is cleavable following entry into said tumor cells.

9. The method of claim 1, wherein said heptamethine cyanine dye comprises one of the following compositions:

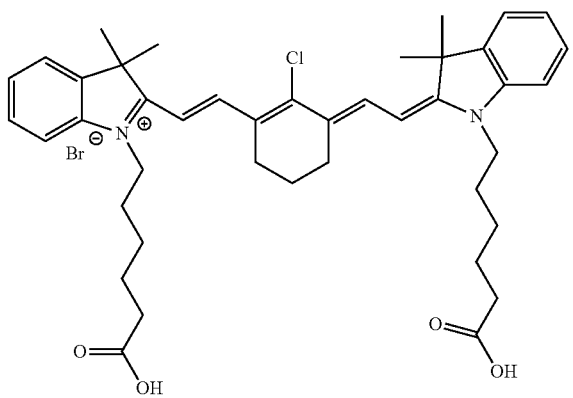

10. The method of claim 1, wherein said heptamethine cyanine dye comprises one of the following compositions:

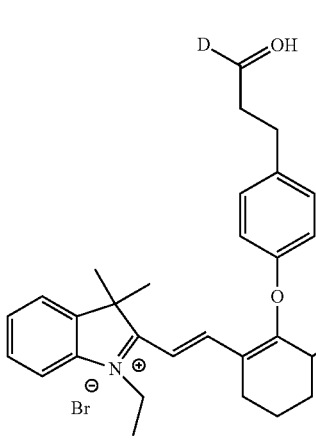

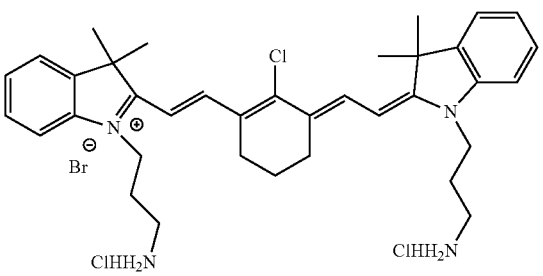

11. The method of claim 1, wherein said conjugate comprises the following composition:

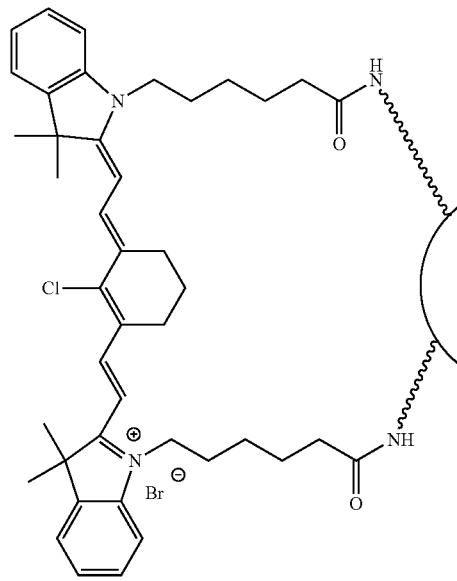
wherein each wavy line represents at least one of said linkers of claim 1.
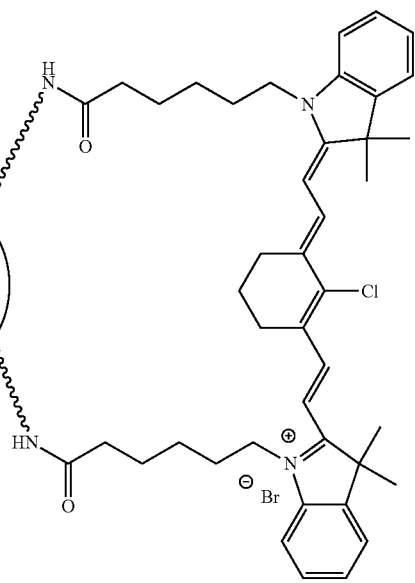
12. The method of claim 1, wherein said conjugate comprises one of the following compositions:
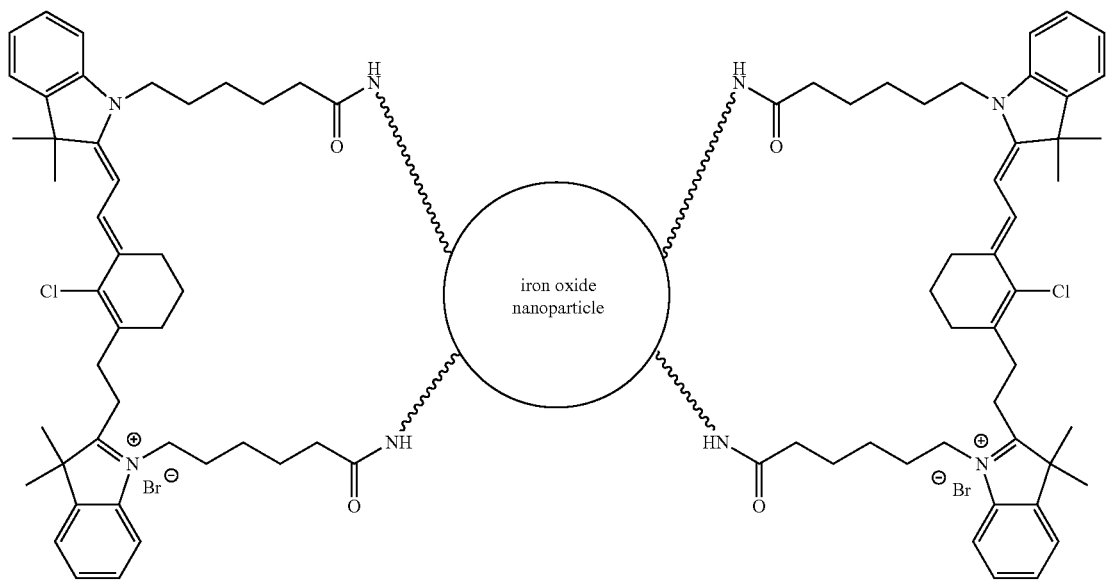

-continued
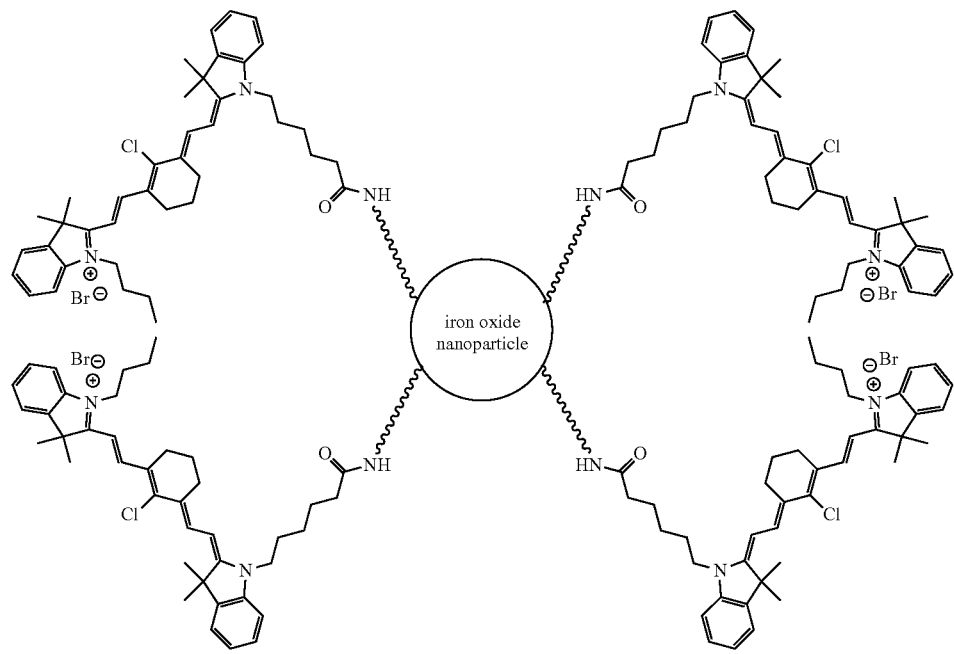
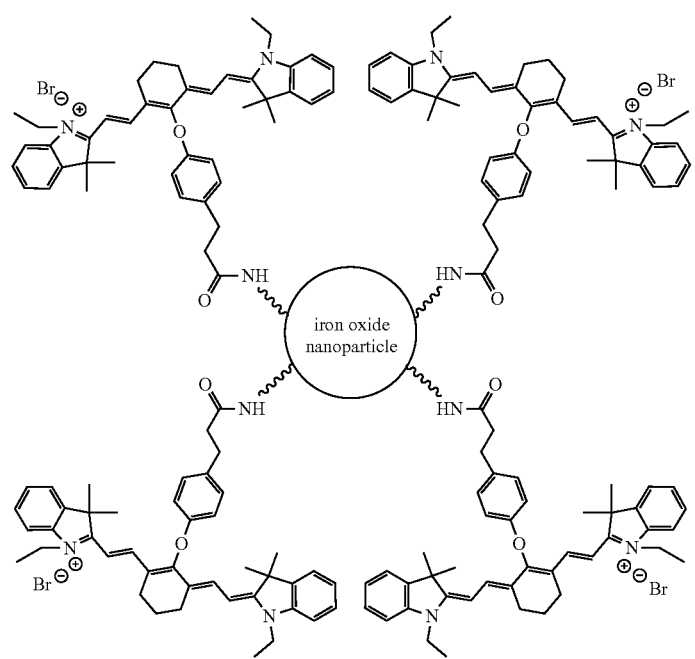

-continued
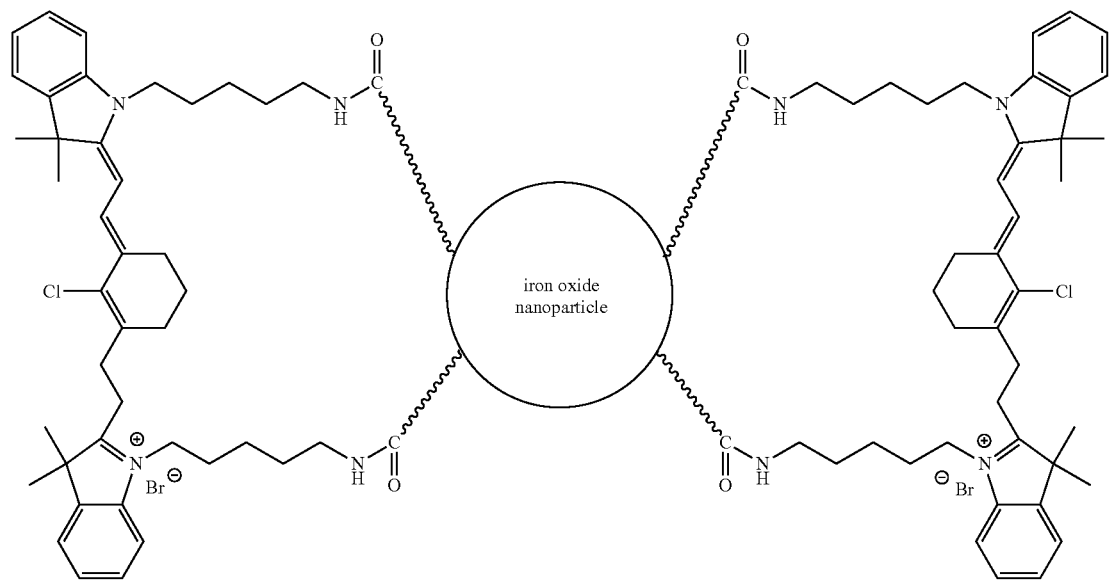
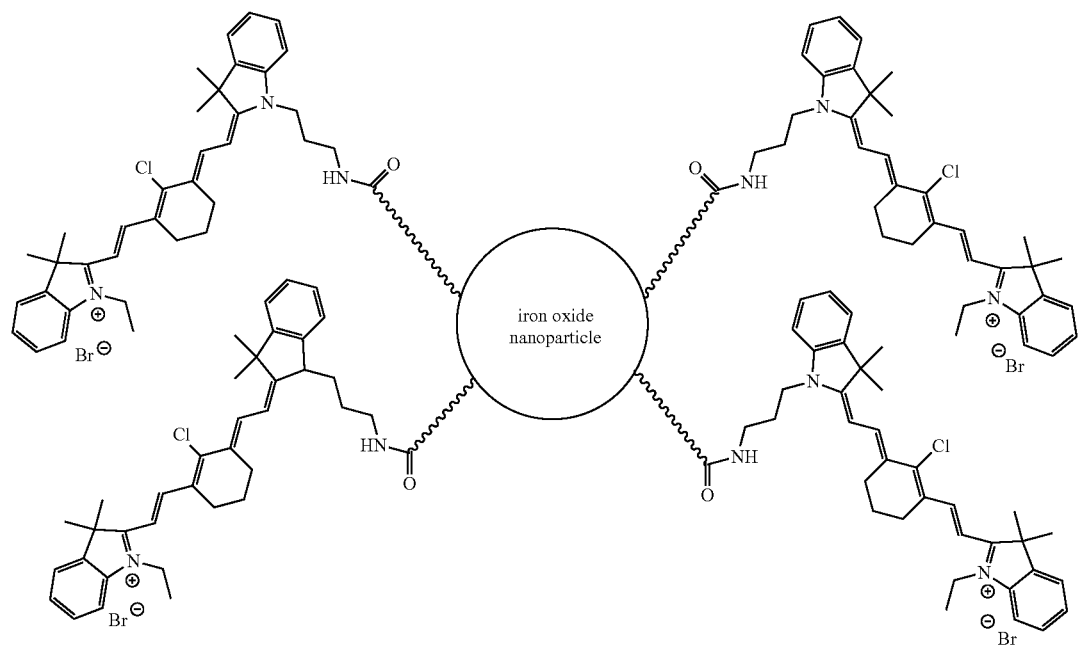

-continued
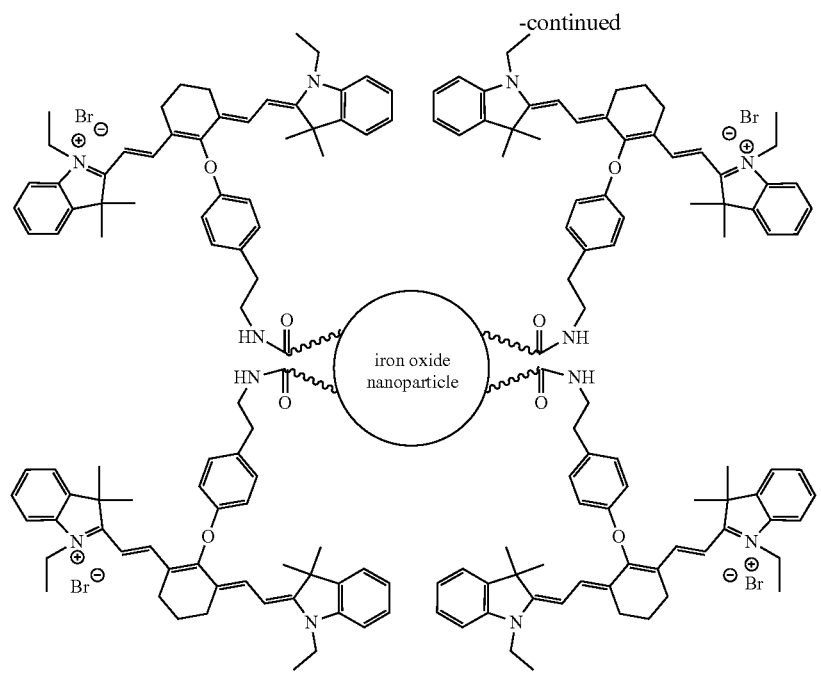
wherein each wavy line represents at least one of said linkers of claim 1.
* * * * *